(12) United States Patent
Nunn et al.

(10) Patent No.: US 10,716,512 B2
(45) Date of Patent: *Jul. 21, 2020

(54) BED WITH USER OCCUPANCY TRACKING

(71) Applicant: Sleep Number Corporation, Minneapolis, MN (US)

(72) Inventors: Rob Nunn, Eden Prairie, MN (US); Wade Daniel Palashewski, Andover, MN (US); Robert Erko, Apple Valley, MN (US)

(73) Assignee: Sleep Number Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/141,068

(22) Filed: Sep. 25, 2018

(65) Prior Publication Data

US 2019/0029597 A1    Jan. 31, 2019

Related U.S. Application Data

(63) Continuation of application No. 14/988,428, filed on Jan. 5, 2016, now Pat. No. 10,092,242.

(60) Provisional application No. 62/099,916, filed on Jan. 5, 2015.

(51) Int. Cl.
| | | |
|---|---|---|
| *A47C 27/08* | (2006.01) | |
| *A61B 5/00* | (2006.01) | |
| *F04D 15/00* | (2006.01) | |
| *F04D 27/00* | (2006.01) | |
| *G05B 15/02* | (2006.01) | |

(52) U.S. Cl.
CPC .......... *A61B 5/6891* (2013.01); *A47C 27/083* (2013.01); *F04D 15/0088* (2013.01); *F04D 27/001* (2013.01); *G05B 15/02* (2013.01); *G05B 2219/2642* (2013.01)

(58) Field of Classification Search
CPC . A47C 27/083; A61B 5/6891; F04D 15/0088; F04D 27/001; G05B 15/02; G05B 2219/2642
See application file for complete search history.

(56) References Cited

U.S. PATENT DOCUMENTS

| | | | |
|---|---|---|---|
| 3,727,606 | A | 4/1973 | Sielaff |
| 4,146,885 | A | 3/1979 | Lawson, Jr. |
| 4,299,233 | A | 11/1981 | Lemelson |
| 4,438,771 | A | 3/1984 | Friesen et al. |
| 4,657,026 | A | 4/1987 | Tagg |
| 4,662,012 | A | 5/1987 | Tarbet |
| 4,766,628 | A | 8/1988 | Walker |

(Continued)

FOREIGN PATENT DOCUMENTS

| | | |
|---|---|---|
| DE | 40 05 822 | 8/1991 |
| GB | 2 471 401 | 12/2010 |

(Continued)

OTHER PUBLICATIONS

U.S. Appl. No. 14/146,281, filed Jan. 2, 2014, Palashewski et al.

(Continued)

*Primary Examiner* — Abdelmoniem I Elamin
(74) *Attorney, Agent, or Firm* — Fish & Richardson P.C.

(57) ABSTRACT

If a user enters a bed, a sensor in the pump of the bed can detect the user's presence in the bed.

20 Claims, 12 Drawing Sheets

(56) References Cited

U.S. PATENT DOCUMENTS

| | | |
|---|---|---|
| 4,788,729 A | 12/1988 | Walker |
| D300,194 S | 3/1989 | Walker |
| 4,829,616 A | 5/1989 | Walker |
| 4,890,344 A | 1/1990 | Walker |
| 4,897,890 A | 2/1990 | Walker |
| 4,908,895 A | 3/1990 | Walker |
| D313,973 S | 1/1991 | Walker |
| 4,982,466 A | 1/1991 | Higgins et al. |
| 4,991,244 A | 2/1991 | Walker |
| 5,020,176 A | 6/1991 | Dotson |
| 5,062,169 A | 11/1991 | Kennedy et al. |
| 5,144,706 A | 9/1992 | Walker et al. |
| 5,170,522 A | 12/1992 | Walker |
| 5,197,490 A | 3/1993 | Steiner et al. |
| 5,459,452 A | 10/1995 | DePonte |
| 5,487,196 A | 1/1996 | Wilkinson et al. |
| D368,475 S | 4/1996 | Scott |
| 5,509,154 A | 4/1996 | Shafer et al. |
| 5,515,865 A | 5/1996 | Scanlon |
| 5,564,140 A | 10/1996 | Shoenhair et al. |
| 5,642,546 A | 7/1997 | Shoenhair |
| 5,652,484 A | 7/1997 | Shafer et al. |
| 5,675,855 A | 10/1997 | Culp |
| 5,684,460 A | 11/1997 | Scanlon |
| 5,699,038 A | 12/1997 | Ulrich et al. |
| 5,724,990 A | 3/1998 | Ogino |
| 5,765,246 A | 6/1998 | Shoenhair |
| 5,771,511 A | 6/1998 | Kummer et al. |
| 5,796,340 A | 8/1998 | Miller |
| 5,844,488 A | 12/1998 | Musick |
| 5,848,450 A | 12/1998 | Oexman et al. |
| 5,903,941 A | 5/1999 | Shafer et al. |
| 5,904,172 A | 5/1999 | Gifft et al. |
| 5,948,303 A | 9/1999 | Larson |
| 5,964,720 A | 10/1999 | Pelz |
| 5,989,193 A | 11/1999 | Sullivan |
| 6,024,699 A | 2/2000 | Surwit et al. |
| 6,037,723 A | 3/2000 | Shafer et al. |
| 6,058,537 A | 5/2000 | Larson |
| 6,062,216 A | 5/2000 | Corn |
| 6,094,762 A | 8/2000 | Viard et al. |
| 6,108,844 A | 8/2000 | Kraft et al. |
| 6,120,441 A | 9/2000 | Griebel |
| 6,146,332 A | 11/2000 | Pinsonneault et al. |
| 6,147,592 A | 11/2000 | Ulrich et al. |
| 6,161,231 A | 12/2000 | Kraft et al. |
| 6,202,239 B1 | 3/2001 | Ward et al. |
| 6,208,250 B1 | 3/2001 | Dixon et al. |
| 6,234,642 B1 | 5/2001 | Bokaemper |
| 6,272,378 B1 | 8/2001 | Baumgart-Schmitt |
| 6,386,201 B1 | 5/2002 | Fard |
| 6,396,224 B1 | 5/2002 | Luff et al. |
| 6,397,419 B1 | 6/2002 | Mechache |
| 6,438,776 B2 | 8/2002 | Ferrand et al. |
| 6,450,957 B1 | 9/2002 | Yoshimi et al. |
| 6,468,234 B1 | 10/2002 | Ford et al. |
| 6,483,264 B1 | 11/2002 | Shafer et al. |
| 6,485,441 B2 | 11/2002 | Woodward |
| 6,546,580 B2 | 4/2003 | Shimada |
| 6,547,743 B2 | 4/2003 | Brydon |
| 6,561,047 B1 | 5/2003 | Gladney |
| 6,566,833 B2 | 5/2003 | Bartlett |
| 6,686,711 B2 | 2/2004 | Rose et al. |
| 6,708,357 B2 | 3/2004 | Gaboury et al. |
| 6,719,708 B1 | 4/2004 | Jansen |
| 6,763,541 B2 | 7/2004 | Mahoney et al. |
| 6,778,090 B2 | 8/2004 | Newham |
| 6,804,848 B1 | 10/2004 | Rose |
| 6,832,397 B2 | 12/2004 | Gaboury et al. |
| 6,840,117 B2 | 1/2005 | Hubbard, Jr. |
| 6,840,907 B1 | 1/2005 | Brydon |
| 6,847,301 B1 | 1/2005 | Olson |
| D502,929 S | 3/2005 | Copeland et al. |
| 6,878,121 B2 | 4/2005 | Krausman |
| 6,883,191 B2 | 4/2005 | Gaboury et al. |
| 6,993,380 B1 | 1/2006 | Modarres |
| 7,041,049 B1 | 5/2006 | Raniere |
| 7,077,810 B2 | 7/2006 | Lange et al. |
| 7,150,718 B2 | 12/2006 | Okada |
| 7,237,287 B2 | 7/2007 | Weismiller et al. |
| 7,253,366 B2 | 8/2007 | Bhai |
| 7,304,580 B2 | 12/2007 | Sullivan et al. |
| 7,314,451 B2 | 1/2008 | Halperin et al. |
| 7,321,811 B1 | 1/2008 | Rawls-Meehan |
| 7,330,127 B2 | 2/2008 | Price et al. |
| 7,389,554 B1 | 6/2008 | Rose |
| 7,396,331 B2 | 7/2008 | Mack |
| 7,429,247 B2 | 9/2008 | Okada et al. |
| 7,437,787 B2 | 10/2008 | Bhai |
| 7,465,280 B2 | 12/2008 | Rawls-Meehan |
| 7,480,951 B2 | 1/2009 | Weismiller |
| 7,506,390 B2 | 3/2009 | Dixon et al. |
| 7,520,006 B2 | 4/2009 | Menkedick et al. |
| 7,524,279 B2 | 4/2009 | Auphan |
| 7,532,934 B2 | 5/2009 | Lee et al. |
| 7,538,659 B2 | 5/2009 | Ulrich |
| 7,568,246 B2 | 8/2009 | Weismiller et al. |
| 7,637,859 B2 | 12/2009 | Lindback et al. |
| 7,652,581 B2 | 1/2010 | Gentry et al. |
| 7,666,151 B2 | 2/2010 | Sullivan et al. |
| 7,669,263 B2 | 3/2010 | Menkedick et al. |
| 7,676,872 B2 | 3/2010 | Block et al. |
| 7,685,663 B2 | 3/2010 | Rawls-Meehan |
| 7,699,784 B2 | 4/2010 | Wan et al. |
| 7,717,848 B2 | 5/2010 | Heruth et al. |
| 7,749,154 B2 | 7/2010 | Cornel |
| 7,784,128 B2 | 8/2010 | Kramer |
| 7,785,257 B2 | 8/2010 | Mack et al. |
| 7,805,785 B2 | 10/2010 | Rawls-Meehan |
| 7,841,031 B2 | 11/2010 | Rawls-Meehan |
| 7,849,545 B2 | 12/2010 | Flocard et al. |
| 7,854,031 B2 | 12/2010 | Rawls-Meehan |
| 7,860,723 B2 | 12/2010 | Rawls-Meehan |
| 7,862,523 B2 | 1/2011 | Ruotoistenmaki |
| 7,865,988 B2 | 1/2011 | Koughan et al. |
| 7,868,757 B2 | 1/2011 | Radivojevic et al. |
| 7,869,903 B2 | 1/2011 | Turner et al. |
| 7,930,783 B2 | 4/2011 | Rawls-Meehan |
| 7,933,669 B2 | 4/2011 | Rawls-Meehan |
| 7,953,613 B2 | 5/2011 | Gizewski |
| 7,954,189 B2 | 6/2011 | Rawls-Meehan |
| 7,956,755 B2 | 6/2011 | Lee et al. |
| 7,967,739 B2 | 6/2011 | Auphan |
| 7,979,169 B2 | 7/2011 | Rawls-Meehan |
| 8,019,486 B2 | 9/2011 | Rawls-Meehan |
| 8,020,230 B2 | 9/2011 | Rawls-Meehan |
| 8,028,363 B2 | 10/2011 | Rawls-Meehan |
| 8,032,263 B2 | 10/2011 | Rawls-Meehan |
| 8,032,960 B2 | 10/2011 | Rawls-Meehan |
| 8,046,114 B2 | 10/2011 | Rawls-Meehan |
| 8,046,115 B2 | 10/2011 | Rawls-Meehan |
| 8,046,116 B2 | 10/2011 | Rawls-Meehan |
| 8,046,117 B2 | 10/2011 | Rawls-Meehan |
| 8,050,805 B2 | 11/2011 | Rawls-Meehan |
| 8,052,612 B2 | 11/2011 | Tang |
| 8,065,764 B2 | 11/2011 | Kramer |
| 8,069,852 B2 | 12/2011 | Burton |
| 8,073,535 B2 | 12/2011 | Jung et al. |
| 8,078,269 B2 | 12/2011 | Suzuki et al. |
| 8,078,336 B2 | 12/2011 | Rawls-Meehan |
| 8,078,337 B2 | 12/2011 | Rawls-Meehan |
| 8,083,682 B2 | 12/2011 | Dalal et al. |
| 8,090,478 B2 | 1/2012 | Skinner et al. |
| 8,092,399 B2 | 1/2012 | Sasaki |
| 8,094,013 B1 | 1/2012 | Lee |
| 8,096,960 B2 | 1/2012 | Loree et al. |
| 8,144,001 B2 | 3/2012 | D'Souza |
| 8,146,191 B2 | 4/2012 | Bobey et al. |
| 8,150,562 B2 | 4/2012 | Rawls-Meehan |
| 8,166,589 B2 | 5/2012 | Hijlkema |
| 8,181,290 B2 | 5/2012 | Brykalski et al. |
| 8,181,296 B2 | 5/2012 | Rawls-Meehan |
| 8,266,742 B2 | 9/2012 | Andrienko |
| 8,272,892 B2 | 9/2012 | McNeely et al. |

(56) References Cited

U.S. PATENT DOCUMENTS

| | | | |
|---|---|---|---|
| 8,276,585 B2 | 10/2012 | Buckley | |
| 8,279,057 B2 | 10/2012 | Hirose | |
| 8,280,748 B2 | 10/2012 | Allen | |
| 8,281,433 B2 | 10/2012 | Riley et al. | |
| 8,282,452 B2 | 10/2012 | Grigsby et al. | |
| 8,284,047 B2 | 10/2012 | Collins, Jr. | |
| 8,287,452 B2 | 10/2012 | Young et al. | |
| 8,336,369 B2 | 12/2012 | Mahoney | |
| 8,341,784 B2 | 1/2013 | Scott et al. | |
| 8,341,786 B2 | 1/2013 | Oexman et al. | |
| 8,348,840 B2 | 1/2013 | Heit et al. | |
| 8,350,709 B2 | 1/2013 | Receveur | |
| 8,375,488 B2 | 2/2013 | Rawls-Meehan | |
| 8,376,954 B2 | 2/2013 | Lange et al. | |
| 8,382,484 B2 | 2/2013 | Wetmore et al. | |
| 8,386,008 B2 | 2/2013 | Yuen et al. | |
| 8,398,538 B2 | 3/2013 | Dothie | |
| 8,403,865 B2 | 3/2013 | Halperin et al. | |
| 8,413,274 B2 | 4/2013 | Weismiller et al. | |
| 8,421,606 B2 | 4/2013 | Collins, Jr. et al. | |
| 8,428,696 B2 | 4/2013 | Foo | |
| 8,444,558 B2 | 5/2013 | Young et al. | |
| 8,517,953 B2 | 8/2013 | Lange et al. | |
| D691,118 S | 10/2013 | Ingham et al. | |
| 8,620,615 B2 | 12/2013 | Oexman | |
| D697,874 S | 1/2014 | Stusynski et al. | |
| D698,338 S | 1/2014 | Ingham | |
| D701,536 S | 3/2014 | Sakal | |
| 8,672,853 B2 | 3/2014 | Young | |
| 8,679,034 B2 | 3/2014 | Halperin et al. | |
| 8,745,788 B2 | 6/2014 | Bhai | |
| 8,769,747 B2 | 7/2014 | Mahoney et al. | |
| 8,782,830 B2 | 7/2014 | Brykalski et al. | |
| 8,810,379 B2 * | 8/2014 | Murphy | F21V 23/0442 340/286.07 |
| 8,840,564 B2 | 9/2014 | Pinhas et al. | |
| 8,893,339 B2 | 11/2014 | Fleury | |
| 8,931,329 B2 | 1/2015 | Mahoney et al. | |
| 8,966,689 B2 | 3/2015 | McGuire et al. | |
| 8,973,183 B1 | 3/2015 | Palashewski et al. | |
| 8,984,687 B2 | 3/2015 | Stusynski et al. | |
| D737,250 S | 8/2015 | Ingham et al. | |
| 9,131,781 B2 | 9/2015 | Zaiss et al. | |
| 9,293,026 B2 * | 3/2016 | Murphy | F21V 23/0442 |
| 9,370,457 B2 | 6/2016 | Nunn et al. | |
| 9,392,879 B2 | 7/2016 | Nunn et al. | |
| 9,510,688 B2 * | 12/2016 | Nunn | A47C 27/083 |
| 9,635,953 B2 * | 5/2017 | Nunn | A47C 27/083 |
| 9,730,524 B2 | 8/2017 | Chen et al. | |
| 9,737,154 B2 | 8/2017 | Mahoney et al. | |
| 9,770,114 B2 | 9/2017 | Brosnan et al. | |
| D809,843 S | 2/2018 | Keeley et al. | |
| D812,393 S | 3/2018 | Karschnik et al. | |
| 9,924,813 B1 | 3/2018 | Basten et al. | |
| 10,058,467 B2 | 8/2018 | Stusynski et al. | |
| 10,092,242 B2 * | 10/2018 | Nunn | A61B 5/6891 |
| 10,143,312 B2 | 12/2018 | Brosnan et al. | |
| 10,149,549 B2 | 12/2018 | Erko et al. | |
| 10,182,661 B2 | 1/2019 | Nunn et al. | |
| 10,194,752 B2 | 2/2019 | Zaiss et al. | |
| 10,194,753 B2 | 2/2019 | Fleury et al. | |
| 10,201,234 B2 | 2/2019 | Nunn et al. | |
| 10,251,490 B2 | 4/2019 | Nunn et al. | |
| 10,342,358 B1 | 7/2019 | Palashewski et al. | |
| 2002/0124311 A1 | 9/2002 | Peftoulidis | |
| 2003/0045806 A1 | 3/2003 | Brydon | |
| 2003/0128125 A1 | 6/2003 | Burbank et al. | |
| 2003/0166995 A1 | 9/2003 | Jansen | |
| 2003/0182728 A1 | 10/2003 | Chapman et al. | |
| 2003/0221261 A1 | 12/2003 | Tarbet et al. | |
| 2004/0049132 A1 | 3/2004 | Barron et al. | |
| 2005/0022606 A1 | 2/2005 | Partin et al. | |
| 2005/0038326 A1 | 2/2005 | Mathur | |
| 2005/0115561 A1 | 6/2005 | Stahmann et al. | |
| 2005/0190068 A1 | 9/2005 | Gentry et al. | |
| 2005/0283039 A1 | 12/2005 | Cornel | |
| 2006/0020178 A1 | 1/2006 | Sotos et al. | |
| 2006/0031996 A1 | 2/2006 | Rawls-Meehan | |
| 2006/0047217 A1 | 3/2006 | Mirtalebi | |
| 2006/0152378 A1 | 7/2006 | Lokhorst | |
| 2006/0162074 A1 | 7/2006 | Bader | |
| 2007/0118054 A1 | 5/2007 | Pinhas et al. | |
| 2007/0149883 A1 | 6/2007 | Yesha | |
| 2007/0179334 A1 | 8/2007 | Groves et al. | |
| 2007/0180047 A1 | 8/2007 | Dong et al. | |
| 2007/0180618 A1 | 8/2007 | Weismiller et al. | |
| 2007/0276202 A1 | 11/2007 | Raisanen et al. | |
| 2008/0052837 A1 | 3/2008 | Blumberg | |
| 2008/0071200 A1 | 3/2008 | Rawls-Meehan | |
| 2008/0077020 A1 | 3/2008 | Young et al. | |
| 2008/0092291 A1 | 4/2008 | Rawls-Meehan | |
| 2008/0092292 A1 | 4/2008 | Rawls-Meehan | |
| 2008/0092293 A1 | 4/2008 | Rawls-Meehan | |
| 2008/0092294 A1 | 4/2008 | Rawls-Meehan | |
| 2008/0093784 A1 | 4/2008 | Rawls-Meehan | |
| 2008/0097774 A1 | 4/2008 | Rawls-Meehan | |
| 2008/0097778 A1 | 4/2008 | Rawls-Meehan | |
| 2008/0097779 A1 | 4/2008 | Rawls-Meehan | |
| 2008/0104750 A1 | 5/2008 | Rawls-Meehan | |
| 2008/0104754 A1 | 5/2008 | Rawls-Meehan | |
| 2008/0104755 A1 | 5/2008 | Rawls-Meehan | |
| 2008/0104756 A1 | 5/2008 | Rawls-Meehan | |
| 2008/0104757 A1 | 5/2008 | Rawls-Meehan | |
| 2008/0104758 A1 | 5/2008 | Rawls-Meehan | |
| 2008/0104759 A1 | 5/2008 | Rawls-Meehan | |
| 2008/0104760 A1 | 5/2008 | Rawls-Meehan | |
| 2008/0104761 A1 | 5/2008 | Rawls-Meehan | |
| 2008/0109959 A1 | 5/2008 | Rawls-Meehan | |
| 2008/0109964 A1 | 5/2008 | Flocard et al. | |
| 2008/0109965 A1 | 5/2008 | Mossbeck | |
| 2008/0115272 A1 | 5/2008 | Rawls-Meehan | |
| 2008/0115273 A1 | 5/2008 | Rawls-Meehan | |
| 2008/0115274 A1 | 5/2008 | Rawls-Meehan | |
| 2008/0115275 A1 | 5/2008 | Rawls-Meehan | |
| 2008/0115276 A1 | 5/2008 | Rawls-Meehan | |
| 2008/0115277 A1 | 5/2008 | Rawls-Meehan | |
| 2008/0115278 A1 | 5/2008 | Rawls-Meehan | |
| 2008/0115279 A1 | 5/2008 | Rawls-Meehan | |
| 2008/0115280 A1 | 5/2008 | Rawls-Meehan | |
| 2008/0115281 A1 | 5/2008 | Rawls-Meehan | |
| 2008/0115282 A1 | 5/2008 | Rawls-Meehan | |
| 2008/0120775 A1 | 5/2008 | Rawls-Meehan | |
| 2008/0120776 A1 | 5/2008 | Rawls-Meehan | |
| 2008/0120777 A1 | 5/2008 | Rawls-Meehan | |
| 2008/0120778 A1 | 5/2008 | Rawls-Meehan | |
| 2008/0120779 A1 | 5/2008 | Rawls-Meehan | |
| 2008/0120784 A1 | 5/2008 | Warner et al. | |
| 2008/0122616 A1 | 5/2008 | Warner | |
| 2008/0126122 A1 | 5/2008 | Warner et al. | |
| 2008/0126132 A1 | 5/2008 | Warner | |
| 2008/0127418 A1 | 6/2008 | Rawls-Meehan | |
| 2008/0127424 A1 | 6/2008 | Rawls-Meehan | |
| 2008/0132808 A1 | 6/2008 | Lokhorst et al. | |
| 2008/0147442 A1 | 6/2008 | Warner | |
| 2008/0162171 A1 | 7/2008 | Rawls-Meehan | |
| 2008/0169931 A1 * | 7/2008 | Gentry | A61B 5/1113 340/573.1 |
| 2008/0189865 A1 * | 8/2008 | Bhai | A61G 7/05769 5/706 |
| 2008/0275314 A1 | 11/2008 | Mack et al. | |
| 2008/0281611 A1 | 11/2008 | Rawls-Meehan | |
| 2008/0281612 A1 | 11/2008 | Rawls-Meehan | |
| 2008/0281613 A1 | 11/2008 | Rawls-Meehan | |
| 2008/0288272 A1 | 11/2008 | Rawls-Meehan | |
| 2008/0288273 A1 | 11/2008 | Rawls-Meehan | |
| 2008/0306351 A1 | 12/2008 | Izumi | |
| 2008/0307582 A1 | 12/2008 | Flocard et al. | |
| 2009/0018853 A1 | 1/2009 | Rawls-Meehan | |
| 2009/0018854 A1 | 1/2009 | Rawls-Meehan | |
| 2009/0018855 A1 | 1/2009 | Rawls-Meehan | |
| 2009/0018856 A1 | 1/2009 | Rawls-Meehan | |
| 2009/0018857 A1 | 1/2009 | Rawls-Meehan | |
| 2009/0018858 A1 | 1/2009 | Rawls-Meehan | |
| 2009/0024406 A1 | 1/2009 | Rawls-Meehan | |

(56) References Cited

U.S. PATENT DOCUMENTS

| | | |
|---|---|---|
| 2009/0037205 A1 | 2/2009 | Rawls-Meehan |
| 2009/0043595 A1 | 2/2009 | Rawls-Meehan |
| 2009/0064420 A1 | 3/2009 | Rawls-Meehan |
| 2009/0100599 A1 | 4/2009 | Rawls-Meehan |
| 2009/0121660 A1 | 5/2009 | Rawls-Meehan |
| 2009/0139029 A1 | 6/2009 | Rawls-Meehan |
| 2009/0203972 A1 | 8/2009 | Henehgan et al. |
| 2009/0275808 A1 | 11/2009 | DiMaio et al. |
| 2009/0314354 A1 | 12/2009 | Chaffee |
| 2010/0025900 A1 | 2/2010 | Rawls-Meehan |
| 2010/0090383 A1 | 4/2010 | Rawls-Meehan |
| 2010/0094139 A1 | 4/2010 | Brauers et al. |
| 2010/0099954 A1 | 4/2010 | Dickinson et al. |
| 2010/0152546 A1 | 6/2010 | Behan et al. |
| 2010/0170043 A1 | 7/2010 | Young et al. |
| 2010/0174198 A1 | 7/2010 | Young et al. |
| 2010/0174199 A1 | 7/2010 | Young et al. |
| 2010/0191136 A1 | 7/2010 | Wolford |
| 2010/0199432 A1 | 8/2010 | Rawls-Meehan |
| 2010/0231421 A1 | 9/2010 | Rawls-Meehan |
| 2010/0302044 A1 | 12/2010 | Chacon et al. |
| 2010/0317930 A1 | 12/2010 | Oexman et al. |
| 2011/0001622 A1 | 1/2011 | Gentry |
| 2011/0010014 A1 | 1/2011 | Oexman et al. |
| 2011/0015495 A1 | 1/2011 | Dothie et al. |
| 2011/0041592 A1 | 2/2011 | Schmoeller et al. |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0144455 A1 | 6/2011 | Young et al. |
| 2011/0156915 A1 | 6/2011 | Brauers et al. |
| 2011/0163885 A1 | 7/2011 | Poulos et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman et al. |
| 2011/0295083 A1 | 12/2011 | Doelling et al. |
| 2011/0302720 A1 | 12/2011 | Yakam et al. |
| 2012/0025992 A1 | 2/2012 | Tallent et al. |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0090698 A1 | 4/2012 | Giori et al. |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1 | 6/2012 | Rawls-Meehan |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0311790 A1 | 12/2012 | Nomura et al. |
| 2013/0074262 A1 | 3/2013 | Receveur et al. |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2013/0283530 A1 | 10/2013 | Main et al. |
| 2014/0007656 A1 | 1/2014 | Mahoney |
| 2014/0009293 A1 | 1/2014 | Sauser et al. |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259433 A1 | 9/2014 | Nunn et al. |
| 2014/0259434 A1* | 9/2014 | Nunn ................ A47C 27/083 5/713 |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0007393 A1 | 1/2015 | Palashewski |
| 2015/0008710 A1 | 1/2015 | Young et al. |
| 2015/0025327 A1 | 1/2015 | Young et al. |
| 2015/0026896 A1 | 1/2015 | Fleury et al. |
| 2015/0136146 A1 | 5/2015 | Hood et al. |
| 2015/0157137 A1 | 6/2015 | Nunn et al. |
| 2015/0157519 A1 | 6/2015 | Stusynski et al. |
| 2015/0182033 A1 | 7/2015 | Brosnan et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |
| 2016/0005288 A1* | 1/2016 | Murphy ............. F21V 23/0442 340/573.4 |
| 2016/0100696 A1* | 4/2016 | Palashewski ........ A47C 31/00 700/90 |
| 2016/0242562 A1* | 8/2016 | Karschnik ........... A47C 27/084 |
| 2016/0338871 A1 | 11/2016 | Nunn et al. |
| 2016/0367039 A1 | 12/2016 | Young et al. |
| 2017/0003666 A1 | 1/2017 | Nunn et al. |
| 2017/0049243 A1* | 2/2017 | Nunn ................ A47C 27/083 |
| 2017/0191516 A1 | 7/2017 | Griffith et al. |
| 2017/0231577 A1* | 8/2017 | Ben Shalom ......... G16H 50/30 600/595 |
| 2017/0303697 A1 | 10/2017 | Chen et al. |
| 2017/0318980 A1 | 11/2017 | Mahoney et al. |
| 2017/0354268 A1 | 12/2017 | Brosnan et al. |
| 2018/0116415 A1 | 5/2018 | Karschnik et al. |
| 2018/0116418 A1 | 5/2018 | Shakal et al. |
| 2018/0116419 A1 | 5/2018 | Shakal et al. |
| 2018/0116420 A1 | 5/2018 | Shakal |
| 2018/0119686 A1 | 5/2018 | Shakal et al. |
| 2018/0125259 A1 | 5/2018 | Peterson et al. |
| 2018/0125260 A1 | 5/2018 | Peterson et al. |
| 2019/0059603 A1 | 2/2019 | Griffith et al. |
| 2019/0082855 A1 | 3/2019 | Brosnan et al. |
| 2019/0104858 A1 | 4/2019 | Erko et al. |
| 2019/0125095 A1 | 5/2019 | Nunn et al. |
| 2019/0125097 A1 | 5/2019 | Nunn et al. |
| 2019/0200777 A1 | 7/2019 | Demirli et al. |
| 2019/0201265 A1 | 7/2019 | Sayadi et al. |
| 2019/0201266 A1 | 7/2019 | Sayadi et al. |
| 2019/0201267 A1 | 7/2019 | Demirli et al. |
| 2019/0201268 A1 | 7/2019 | Sayadi et al. |
| 2019/0201269 A1 | 7/2019 | Sayadi et al. |
| 2019/0201270 A1 | 7/2019 | Sayadi et al. |
| 2019/0201271 A1 | 7/2019 | Grey et al. |
| 2019/0206416 A1 | 7/2019 | Demirli et al. |
| 2019/0209405 A1 | 7/2019 | Sayadi et al. |
| 2019/0279745 A1 | 9/2019 | Sayadi et al. |

FOREIGN PATENT DOCUMENTS

| | | |
|---|---|---|
| JP | 2004/049388 | 2/2004 |
| JP | 2004/229875 | 8/2004 |
| WO | WO 2004/082549 | 9/2004 |
| WO | WO 2008/128250 | 10/2008 |
| WO | WO 2009/108228 | 9/2009 |
| WO | WO 2009/123641 | 10/2009 |
| WO | WO 2010/149788 | 12/2010 |

OTHER PUBLICATIONS

U.S. Appl. No. 15/806,810, filed Nov. 8, 2017, Gaunt.
U.S. Appl. No. 16/122,480, filed Sep. 5, 2018, Shutes et al.
U.S. Appl. No. 16/505,062, filed Jul. 8, 2019, Palashewski et al.
U.S. Appl. No. 29/583,852, filed Nov. 9, 2016, Keeley.
U.S. Appl. No. 29/676,117, filed Jan. 8, 2019, Stusynski et al.
U.S. Appl. No. 29/690,492, filed May 8, 2019, Stusynski et al.

(56) References Cited

OTHER PUBLICATIONS

International Search Report and Written Opinion in International Application No. PCT/US2014/012206, dated Apr. 19, 2016, 21 pages.
International Preliminary Report on Patentability in Application No. PCT/US2016/012206, dated Jul. 11, 2017, 16 pages.

* cited by examiner

BED WITH USER OCCUPANCY TRACKING

CROSS-REFERENCE TO RELATED APPLICATIONS

This application is a continuation of U.S. application Ser. No. 14/988,428, filed Jan. 5, 2016, which claims priority to U.S. Provisional Application Ser. No. 62/099,916, entitled "Bed with User Occupancy Tracking," filed on Jan. 5, 2015, now U.S. Pat. No. 10,092,242, the entire contents of which are incorporated by reference.

BACKGROUND

A computer network is a collection of computers and other hardware interconnected by communication channels that allow sharing of resources and information. Communication protocols define the rules and data formats for exchanging information in a computer network.

In general, a bed is a piece of furniture used as a location to sleep or relax. Many modern beds include a soft mattress on a bed frame. The mattress may include springs, foam material, and/or an air bladder to support the weight of one or more occupants.

SUMMARY

In one aspect, a method performed by data processing apparatuses, the method includes determining, by a computing device, that a mattress is unoccupied. The method further includes receiving, from a mattress pump and at a computing device, a stream of pump pressure readings, the pump pressure readings recording the air pressure of the mattress. The method further includes identifying, by the computing device, an increase in pump pressure readings within a time window. The method further includes after identifying the increase in pump pressure readings within the time window and for each received pump pressure readings, until the computing device determines that a difference is less than a threshold value: calculating, by the computing device, a trailing average pressure that represents the average of the N most recent pump pressure readings in the stream of pump pressure readings. The method further includes determining, by the computing device, the difference between the received pump pressure reading and the trailing average pressure. The method further includes responsive to the computing device determining that the difference is less than the threshold value, performing one of the group consisting of: issuing a presence event, storing a value in computer readable memory, and engaging a peripheral device.

Implementations can include any, all, or none of the following features. Responsive to the computing device determining that the difference is less than the threshold value, performing one of the group consisting of: issuing a presence event, storing a value in computer readable memory, and engaging a peripheral device includes determining that the mattress is occupied for a threshold period of time. Responsive to the computing device determining that the difference is less than the threshold value, performing one of the group consisting of: issuing a presence event, storing a value in computer readable memory, and engaging a peripheral device includes determining that the time of day is within a particular window of time. The particular window of time is determined from historical data. Responsive to the computing device determining that the difference is less than the threshold value, performing one of the group consisting of: issuing a presence event, storing a value in computer readable memory, and engaging a peripheral device includes determining that the user is asleep on the mattress. The method including identifying, based on the stream of pump pressure readings, a supplemental indication of presence in the bed; and wherein, responsive to the computing device determining that the test value is greater than the threshold value, issuing a presence event, storing a value in computer readable memory, engaging a peripheral device further includes combining the supplemental indication of presence in the bed with the determining that the difference is less than the threshold value. The supplemental indication of presence in the bed includes identifying biological activity by an occupant of the bed. The method including modifying the threshold value. The threshold value is modified to account for seasonality. The threshold value is modified to account for growth of the user. The method including updating a user-facing computer interface to show that a user is detected in the bed.

In one aspect, a method performed by data processing apparatuses, the method includes determining, by a computing device, that a mattress is unoccupied. The method further includes receiving, from a mattress pump and at a computing device, an empty pump pressure reading, the empty pump pressure reading recording the air pressure of the mattress when the mattress is not subject to pressure from a person. The method further includes receiving, from a mattress pump and at a computing device, a stream of pump pressure readings, the pump pressure readings recording the air pressure of the mattress when the mattress is subject to pressure from an external body. The method further includes for each received pump pressure readings: calculating, by the computing device, a test value that includes the most recent pump pressure reading in the stream of pump pressure readings. The method further includes determining, by the computing device, if the test value is greater than a threshold value that is greater than the empty pump pressure reading. The method further includes responsive to the computing device determining that the test value is greater than the threshold value, performing one of the group consisting of: issuing a presence event, storing a value in computer readable memory, and engaging a peripheral device.

Implementations can include any, all, or none of the following features. The test value is a trailing average pressure that represents the average of the N most recent pump pressure readings in the stream of pump pressure readings. The method including identifying, based on the stream of pump pressure readings, a supplemental indication of presence in the bed; and wherein, responsive to the computing device determining that the test value is greater than the threshold value, performing one of the group consisting of: issuing a presence event, storing a value in computer readable memory, and engaging a peripheral device further includes combining the supplemental indication of presence in the bed with the determining that the difference is less than the threshold value. The supplemental indication of presence in the bed includes identifying biological activity by an occupant of the bed. The method including modifying the threshold value. The threshold value is modified to account for seasonality. The threshold value is modified to account for growth of the user. The method including updating a user-facing computer interface to show that a user is detected in the bed.

In one aspect, a bed system includes a mattress having an air bladder. The system further includes a pressure sensor fluidically connected to the air bladder. The system further includes a controller in communication with the pressure sensors and configured to receive pressure signals from the pressure sensor. The controller is further configured to: determining, by a computing device, that a mattress is unoccupied. The system further includes receiving, from a mattress pump and at a computing device, a stream of pump pressure readings, the pump pressure readings recording the air pressure of the mattress. The system further includes identifying, by the computing device, an increase in pump pressure readings within a time window. The system further includes after identifying the increase in pump pressure readings within the time window and for each received pump pressure readings, until the computing device determines that a difference is less than a threshold value: calculating, by the computing device, a trailing average pressure that represents the average of the N most recent pump pressure readings in the stream of pump pressure readings. The system further includes determining, by the computing device, the difference between the received pump pressure reading and the trailing average pressure. The system further includes, responsive to the computing device determining that the difference is less than the threshold value, performing one of the group consisting of: issuing a presence event, storing a value in computer readable memory, and engaging a peripheral device.

Implementations can include any, all, or none of the following features. The bed system including a pump fluidically connected to the air bladder, wherein the controller includes a pump controller for driving the pump to inflate the air bladder to a desired pressure upon command by a user.

In one aspect, a method of determining weight of a user on a bed, the method includes sensing pressure in an air bladder of a mattress of the bed via a bed pressure sensor in fluid communication with the air bladder. The method further includes sending a first stream of pressure readings from the bed pressure sensor to a computing device. The method further includes determining, via the computing device and the first stream of pressure readings, that the user is present on the mattress. The method further includes calculating, via the computing device and the first stream of pressure readings, a first weight of the user. The method further includes sending a signal indicative of user weight to a user interface to be displayed as an indicia of user weight by the user interface.

Implementations can include any, all, or none of the following features. The method including sending a second stream of pressure readings from the bed pressure sensor to the computing device; distinguishing, via the computing device, the first stream of pressure readings as indicative of a user positioned on the mattress from the second stream of pressure readings as indicative of one or more objects other than the user being positioned on the mattress; and calculating, via the computing device, the first weight of the user by excluding weight changes due to the one or more objects other than the user. The method including tracking a plurality of user weights over a plurality of days as determined by sensed pressure in the air bladder by the bed pressure sensor; and outputting via a user interface historical weight data of the user over the plurality of days. The computing device adjusts for weight changes due to inanimate objects being placed on and removed from the mattress so as to omit weight changes due to inanimate objects from the historical weight data outputted via the user interface. The computing device adjusts for weight changes due to inanimate objects being placed on and removed from the mattress so as to omit weight changes due to animate objects from the historical weight data outputted via the user interface. The computing device identifies the animate object by detection of biological activity.

Implementations can include any, all, or none of the following features.

The systems and processes described here may be used to provide a number of potential advantages. By tracing the instant pressure readings of an air bladder and comparing the instant pressure readings to another value, the occupancy status of a bed may be determined. For example, as a trailing average approaches the instant pressure readings, a computer system may determine that a user is in the bed. Similarly, a smoothed pressure reading may be compared to an adjustable threshold and, if above the threshold, a computer system may determine that a user is in the bed. To improve the accuracy of one or either of these determinations, additional signals may be considered, including monitoring of biological functions (e.g., heart beat or breathing).

Other features, aspects and potential advantages will be apparent from the accompanying description and figures.

DESCRIPTION OF DRAWINGS

Like reference symbols in the various drawings indicate like elements.

DETAILED DESCRIPTION

To detect user presence in a bed, a pump or other device may include a sensor that monitor the pressure of one or more air bladders in the mattress of the bed. When a user enters the bed, the pressure quickly increases, but because the increase is often noisy and influenced by other articles on the bed, a simple threshold comparison may not sufficiently indicate user occupancy. To account for, for example, the reading noise and other influences, one or more tests may be combined to generate a determination of user occupancy.

After determining if a user is occupying the bed, the pump or other controller may take an appropriate action. For example, a computer readable memory value may be change (e.g. set to true) to reflect the determination that a user is in the bed. A control device may, responsive to the memory value change, change the function of a peripheral device. For example, after it is determined that a user is in their bed, a controller may turn off the user's night light, set the user's alarm clock, or manipulate another device.

Figure 1:
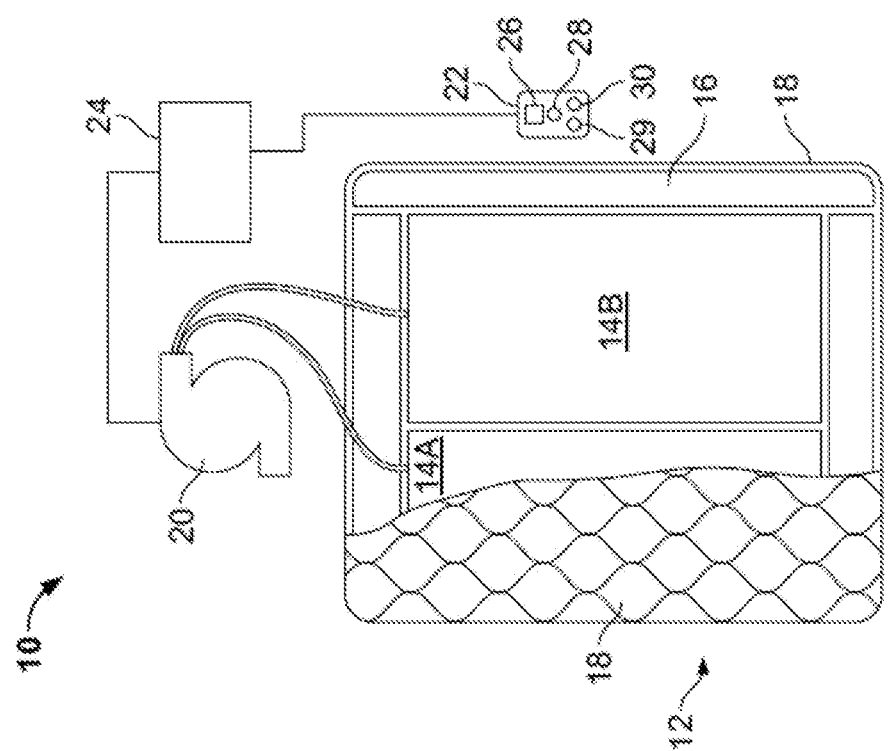
FIG. 1 shows an example air bed system.

FIG. 1 shows an example air bed system 10 that includes a bed 12. The bed 12 includes at least one air chamber 14 surrounded by a resilient border 16 and encapsulated by bed ticking 18. The resilient border 16 may comprise any suitable material, such as foam.

As illustrated in FIG. 1, the bed 12 can be a two chamber design having first and second fluid chambers, such as a first air chamber 14A and a second air chamber 14B. In alternative embodiments, the bed 12 can include chambers for use with fluids other than air that are suitable for the application. In some embodiments, such as single beds or kids' beds, the bed 12 can include a single air chamber 14A or 14B or multiple air chambers 14A and 14B. First and second air chambers 14A and 14B can be in fluid communication with a pump 20. The pump 20 can be in electrical communication with a remote control 22 via control box 24. The control box 24 can include a wired or wireless communications interface for communicating with one or more devices, including the remote control 22. The control box 24 can be configured to operate the pump 20 to cause increases and decreases in the fluid pressure of the first and second air chambers 14A and 14B based upon commands input by a user using the remote control 22. In some implementations, the control box 24 is integrated into a housing of the pump 20.

The remote control 22 may include a display 26, an output selecting mechanism 28, a pressure increase button 29, and a pressure decrease button 30. The output selecting mechanism 28 may allow the user to switch air flow generated by the pump 20 between the first and second air chambers 14A and 14B, thus enabling control of multiple air chambers with a single remote control 22 and a single pump 20. For example, the output selecting mechanism 28 may by a physical control (e.g., switch or button) or an input control displayed on display 26. Alternatively, separate remote control units can be provided for each air chamber and may each include the ability to control multiple air chambers. Pressure increase and decrease buttons 29 and 30 may allow a user to increase or decrease the pressure, respectively, in the air chamber selected with the output selecting mechanism 28. Adjusting the pressure within the selected air chamber may cause a corresponding adjustment to the firmness of the respective air chamber. In some embodiments, the remote control 22 can be omitted or modified as appropriate for an application. For example, in some embodiments the bed 12 can be controlled by a computer, tablet, smart phone, or other device in wired or wireless communication with the bed 12.

Figure 2:
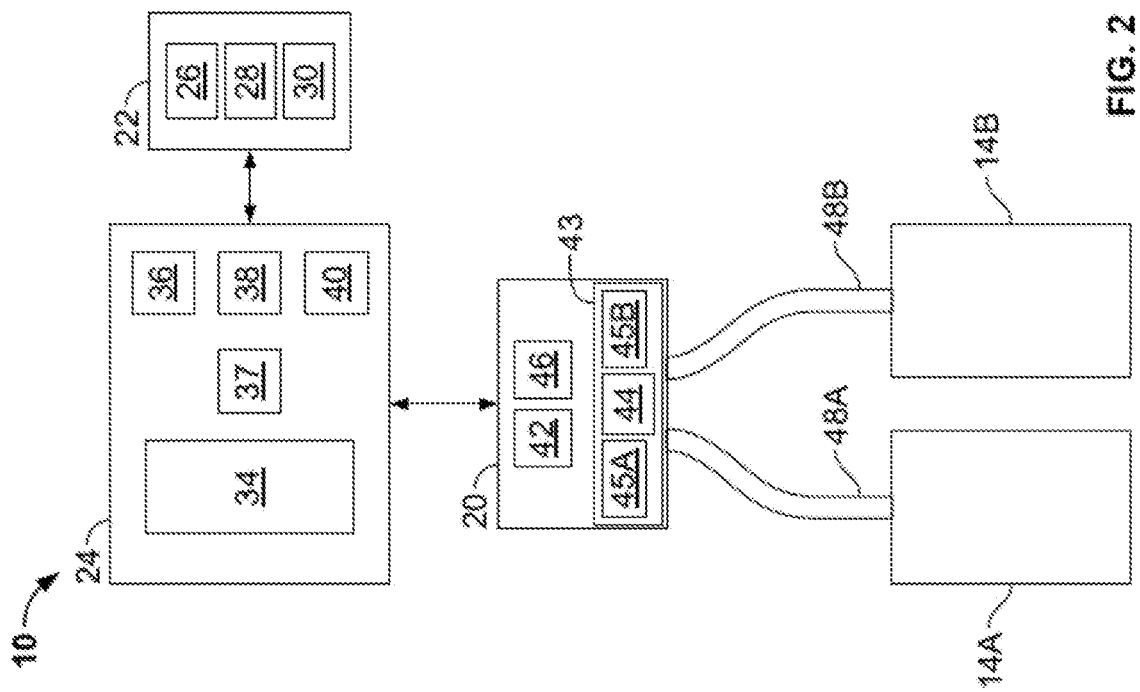
FIG. 2 is a block diagram of various components of the air bed system of FIG. 1, according to an example.

FIG. 2 is a block diagram detailing data communication between certain components of the example air bed system 10 according to various examples. As shown in FIG. 2, the control box 24 may include a power supply 34, a processor 36, a memory 37, a switching mechanism 38, and an analog to digital (A/D) converter 40. The switching mechanism 38 can be, for example, a relay or a solid state switch. In some implementations, the switching mechanism 38 can be located in the pump 20 rather than the control box 24.

The pump 20 and the remote control 22 are in two-way communication with the control box 24. The pump 20 includes a motor 42, a pump manifold 43, a relief valve 44, a first control valve 45A, a second control valve 45B, and a pressure transducer 46. The pump 20 is fluidly connected with the first air chamber 14A and the second air chamber 14B via a first tube 48A and a second tube 48B, respectively. The first and second control valves 45A and 45B can be controlled by switching mechanism 38, and are operable to regulate the flow of fluid between the pump 20 and first and second air chambers 14A and 14B, respectively.

In some implementations, the pump 20 and the control box 24 can be provided and packaged as a single unit. In some alternative implementations, the pump 20 and the control box 24 may be provided as physically separate units. In some implementations, the control box 24, the pump 20, or both are integrated within or otherwise contained within a bed frame or bed support structure that supports the bed 12. In some implementations, the control box 24, the pump 20, or both are located outside of a bed frame or bed support structure (as shown in the example in FIG. 1).

The example air bed system 10 depicted in FIG. 2 includes the two air chambers 14A and 14B and the single pump 20. However, other implementations may include an air bed system having two or more air chambers and one or more pumps incorporated into the air bed system to control the air chambers. For example, a separate pump can be associated with each air chamber of the air bed system or a pump can be associated with multiple chambers of the air bed system. Separate pumps may allow each air chamber to be inflated or deflated independently and simultaneously. Furthermore, additional pressure transducers may also be incorporated into the air bed system such that, for example, a separate pressure transducer can be associated with each air chamber.

In use, the processor 36 can, for example, send a decrease pressure command to one of air chambers 14A or 14B, and the switching mechanism 38 can be used to convert the low voltage command signals sent by the processor 36 to higher operating voltages sufficient to operate the relief valve 44 of the pump 20 and open the control valve 45A or 45B. Opening the relief valve 44 may allow air to escape from the air chamber 14A or 14B through the respective air tube 48A or 48B. During deflation, the pressure transducer 46 may send pressure readings to the processor 36 via the A/D converter 40. The A/D converter 40 may receive analog information from pressure transducer 46 and may convert the analog information to digital information useable by the processor 36. The processor 36 may send the digital signal to the remote control 22 to update the display 26 in order to convey the pressure information to the user.

As another example, the processor 36 can send an increase pressure command. The pump motor 42 can be energized in response to the increase pressure command and send air to the designated one of the air chambers 14A and 14B through the air tube 48A or 48B via electronically operating the corresponding valve 45A or 45B. While air is being delivered to the designated air chamber 14 A or 14B in order to increase the firmness of the chamber, the pressure transducer 46 may sense pressure within the pump manifold 43. Again, the pressure transducer 46 may send pressure readings to the processor 36 via the A/D converter 40. The processor 36 may use the information received from the A/D converter 40 to determine the difference between the actual pressure in air chamber 14A or 14B and the desired pressure. The processor 36 may send the digital signal to the remote control 22 to update display 26 in order to convey the pressure information to the user.

Generally speaking, during an inflation or deflation process, the pressure sensed within the pump manifold 43 can provide an approximation of the pressure within the respective air chamber that is in fluid communication with the pump manifold 43. An example method of obtaining a pump manifold pressure reading that is substantially equivalent to the actual pressure within an air chamber includes turning off pump 20, allowing the pressure within the air chamber 14A or 14B and the pump manifold 43 to equalize, and then sensing the pressure within the pump manifold 43 with the pressure transducer 46. Thus, providing a sufficient amount of time to allow the pressures within the pump manifold 43 and chamber 14A or 14B to equalize may result in pressure readings that are accurate approximations of the actual pressure within air chamber 14A or 14B. In some implementations, the pressure of the air chambers 14A and/or 14B can be continuously monitored using multiple pressure sensors.

In some implementations, information collected by the pressure transducer 46 can be analyzed to determine various states of a person lying on the bed 12. For example, the processor 36 can use information collected by the pressure transducer 46 to determine a heart rate or a respiration rate for a person lying in the bed 12. For example, a user can be lying on a side of the bed 12 that includes the chamber 14A. The pressure transducer 46 can monitor fluctuations in pressure of the chamber 14A and this information can be used to determine the user's heart rate and/or respiration rate. As another example, additional processing can be performed using the collected data to determine a sleep state of the person (e.g., awake, light sleep, deep sleep). For example, the processor 36 may determine when a person falls asleep and, while asleep, the various sleep states of the person.

Additional information associated with a user of the bed system 10 that can be determined using information collected by the pressure transducer 46 includes motion of the user, presence of the user on a surface of the bed 12, weight of the user, heart arrhythmia of the user, and apnea. Taking user presence detection for example, the pressure transducer 46 can be used to detect the user's presence on the bed 12, e.g., via a gross pressure change determination and/or via one or more of a respiration rate signal, heart rate signal, and/or other biometric signals. For example, a simple pressure detection process can identify an increase in pressure as an indication that the user is present in the bed 12. As another example, the processor 36 can determine that the user is present in the bed 12 if the detected pressure increases above a specified threshold (so as to indicate that a person or other object above a certain weight is positioned on the bed 12). As yet another example, the processor 36 can identify an increase in pressure in combination with detected slight, rhythmic fluctuations in pressure as corresponding to the user being present on the bed 12. The presence of rhythmic fluctuations can be identified as being caused by respiration or heart rhythm (or both) of the user. The detection of respiration or a heartbeat can distinguish between the user being present on the bed and another object (e.g., a suit case) being placed upon the bed.

In some implementations, fluctuations in pressure can be measured at the pump 20. For example, one or more pressure sensors can be located within one or more internal cavities of the pump 20 to detect fluctuations in pressure within the pump 20. The fluctuations in pressure detected at the pump 20 can indicate fluctuations in pressure in one or both of the chambers 14A and 14B. One or more sensors located at the pump 20 can be in fluid communication with the one or both of the chambers 14A and 14B, and the sensors can be operative to determine pressure within the chambers 14A and 14B. The control box 24 can be configured to determine at least one vital sign (e.g., heart rate, respiratory rate) based on the pressure within the chamber 14A or the chamber 14B.

In some implementations, the control box 24 can analyze a pressure signal detected by one or more pressure sensors to determine a heart rate, respiration rate, and/or other vital signs of a user lying or sitting on the chamber 14A or the chamber 14B. More specifically, when a user lies on the bed 12 positioned over the chamber 14A, each of the user's heart beats, breaths, and other movements can create a force on the bed 12 that is transmitted to the chamber 14A. As a result of the force input to the chamber 14A from the user's movement, a wave can propagate through the chamber 14A and into the pump 20. A pressure sensor located at the pump 20 can detect the wave, and thus the pressure signal output by the sensor can indicate a heart rate, respiratory rate, or other information regarding the user.

With regard to sleep state, system 10 can determine a user's sleep state by using various biometric signals such as heart rate, respiration, and/or movement of the user. While the user is sleeping, the processor 36 can receive one or more of the user's biometric signals (e.g., heart rate, respiration, and motion) and determine the user's present sleep state based on the received biometric signals. In some implementations, signals indicating fluctuations in pressure in one or both of the chambers 14A and 14B can be amplified and/or filtered to allow for more precise detection of heart rate and respiratory rate.

The control box 24 can perform a pattern recognition algorithm or other calculation based on the amplified and filtered pressure signal to determine the user's heart rate and respiratory rate. For example, the algorithm or calculation can be based on assumptions that a heart rate portion of the signal has a frequency in the range of 0.5-4.0 Hz and that a respiration rate portion of the signal a has a frequency in the range of less than 1 Hz. The control box 24 can also be configured to determine other characteristics of a user based on the received pressure signal, such as blood pressure, tossing and turning movements, rolling movements, limb movements, weight, the presence or lack or presence of a user, and/or the identity of the user. Techniques for monitoring a user's sleep using heart rate information, respiration rate information, and other user information are disclosed in U.S. Patent Application Publication No. 20100170043 to Steven J. Young et al., titled "APPARATUS FOR MONITORING VITAL SIGNS," the entire contents of which is incorporated herein by reference.

For example, the pressure transducer 46 can be used to monitor the air pressure in the chambers 14A and 14B of the bed 12. If the user on the bed 12 is not moving, the air pressure changes in the air chamber 14A or 14B can be relatively minimal, and can be attributable to respiration and heartbeat. When the user on the bed 12 is moving, however, the air pressure in the mattress may fluctuate by a much larger amount. Thus, the pressure signals generated by the pressure transducer 46 and received by the processor 36 can be filtered and indicated as corresponding to motion, heartbeat, or respiration.

In some implementations, rather than performing the data analysis in the control box 24 with the processor 36, a digital signal processor (DSP) can be provided to analyze the data collected by the pressure transducer 46. Alternatively, the data collected by the pressure transducer 46 could be sent to a cloud-based computing system for remote analysis.

In some implementations, the example air bed system 10 further includes a temperature controller configured to increase, decrease, or maintain the temperature of a user. For example, a pad can be placed on top of or be part of the bed 12, or can be placed on top of or be part of one or both of the chambers 14A and 14B. Air can be pushed through the pad and vented to cool off a user of the bed. Conversely, the pad may include a heating element that can be used to keep the user warm. In some implementations, the temperature controller can receive temperature readings from the pad. In some implementations, separate pads are used for the different sides of the bed 12 (e.g., corresponding to the locations of the chambers 14A and 14B) to provide for differing temperature control for the different sides of the bed.

In some implementations, the user of the system 10 can use an input device, such as the remote control 22, to input a desired temperature for the surface of the bed 12 (or for a portion of the surface of the bed 12). The desired temperature can be encapsulated in a command data structure that includes the desired temperature as well as identifies the temperature controller as the desired component to be controlled. The command data structure may then be transmitted via Bluetooth or another suitable communication protocol to the processor 36. In various examples, the command data structure is encrypted before being transmitted. The temperature controller may then configure its elements to increase or decrease the temperature of the pad depending on the temperature input into remote control 22 by the user.

In some implementations, data can be transmitted from a component back to the processor 36 or to one or more display devices, such as the display 26. For example, the current temperature as determined by a sensor element of temperature controller, the pressure of the bed, the current position of the foundation or other information can be transmitted to control box 24. The control box 24 may then transmit the received information to remote control 22 where it can be displayed to the user (e.g., on the display 26).

In some implementations, the example air bed system 10 further includes an adjustable foundation and an articulation controller configured to adjust the position of a bed (e.g., the bed 12) by adjusting the adjustable foundation that supports the bed. For example, the articulation controller can adjust the bed 12 from a flat position to a position in which a head portion of a mattress of the bed is inclined upward (e.g., to facilitate a user sitting up in bed and/or watching television). In some implementations, the bed 12 includes multiple separately articulable sections. For example, portions of the bed corresponding to the locations of the chambers 14A and 14B can be articulated independently from each other, to allow one person positioned on the bed 12 surface to rest in a first position (e.g., a flat position) while a second person rests in a second position (e.g., an reclining position with the head raised at an angle from the waist). In some implementations, separate positions can be set for two different beds (e.g., two twin beds placed next to each other). The foundation of the bed 12 may include more than one zone that can be independently adjusted. The articulation controller may also be configured to provide different levels of massage to one or more users on the bed 12.

Figure 3:
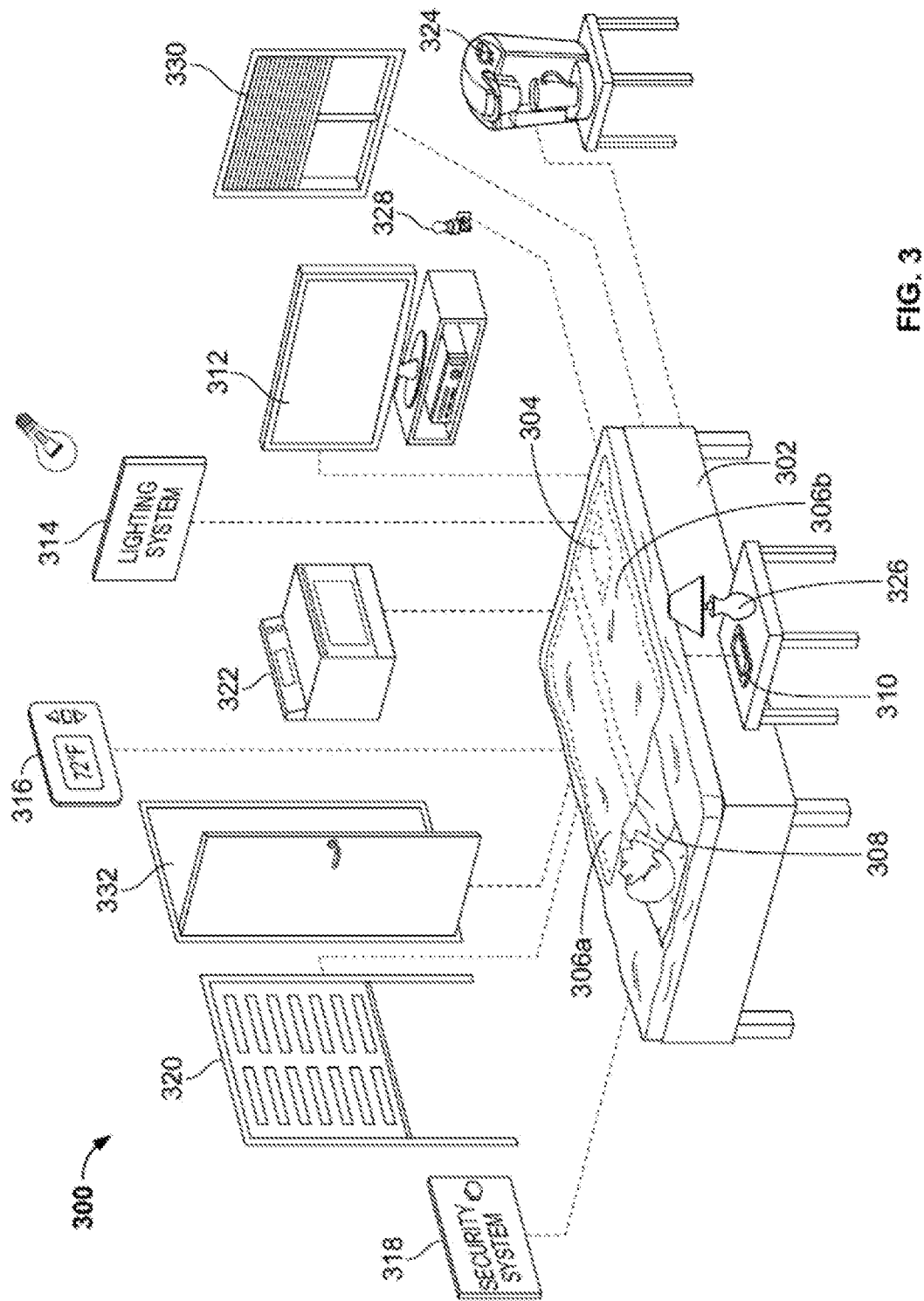
FIG. 3 shows an example environment including a bed in communication with devices located in and around a home.

FIG. 3 shows an example environment 300 including a bed 302 in communication with devices located in and around a home. In the example shown, the bed 302 includes pump 304 for controlling air pressure within two air chambers 306a and 306b (as described above with respect to the air chambers 14A-14B). The pump 304 additionally includes circuitry for controlling inflation and deflation functionality performed by the pump 304. The circuitry is further programmed to detect fluctuations in air pressure of the air chambers 306a-b and used the detected fluctuations in air pressure to identify bed presence of a user 308, sleep state of the user 308, movement of the user 308, and biometric signals of the user 308 such as heart rate and respiration rate. In the example shown, the pump 304 is located within a support structure of the bed 302 and the control circuitry for controlling the pump 304 is integrated with the pump 304. In some implementations, the control circuitry is physically separate from the pump 304 and is in wireless or wired communication with the pump 304. In some implementations, the pump 304 and/or control circuitry are located outside of the bed 302. In some implementations, various control functions can be performed by systems located in different physical locations. For example, circuitry for controlling actions of the pump 304 can be located within a pump casing of the pump 304 while control circuitry for performing other functions associated with the bed 302 can be located in another portion of the bed 302, or external to the bed 302. As another example, control circuitry located within the pump 304 can communicate with control circuitry at a remote location through a LAN or WAN (e.g., the internet). As yet another example, the control circuitry can be included in the control box 24 of FIGS. 1 and 2.

In some implementations, one or more devices other than, or in addition to, the pump 304 and control circuitry can be utilized to identify user bed presence, sleep state, movement, and biometric signals. For example, the bed 302 can include a second pump in addition to the pump 304, with each of the two pumps connected to a respective one of the air chambers 306a-b. For example, the pump 304 can be in fluid communication with the air chamber 306b to control inflation and deflation of the air chamber 306a as well as detect user signals for a user located over the air chamber 306b such as bed presence, sleep state, movement, and biometric signals while the second pump is in fluid communication with the air chamber 306a to control inflation and deflation of the air chamber 306a as well as detect user signals for a user located over the air chamber 306a.

As another example, the bed 302 can include one or more pressure sensitive pads or surface portions that are operable to detect movement, including user presence, user motion, respiration, and heart rate. For example, a first pressure sensitive pad can be incorporated into a surface of the bed 302 over a left portion of the bed 302, where a first user would normally be located during sleep, and a second pressure sensitive pad can be incorporated into the surface of the bed 302 over a right portion of the bed 302, where a second user would normally be located during sleep. The movement detected by the one or more pressure sensitive pads or surface portions can be used by control circuitry to identify user sleep state, bed presence, or biometric signals.

In some implementations, information detected by the bed (e.g., motion information) is processed by control circuitry (e.g., control circuitry integrated with the pump 304) and provided to one or more user devices such as a user device 310 for presentation to the user 308 or to other users. In the example depicted in FIG. 3, the user device 310 is a tablet device; however, in some implementations, the user device 310 can be a personal computer, a smart phone, a smart television (e.g., a television 312), or other user device capable of wired or wireless communication with the control circuitry. The user device 310 can be in communication with control circuitry of the bed 302 through a network or through direct point-to-point communication. For example, the control circuitry can be connected to a LAN (e.g., through a WiFi router) and communicate with the user device 310 through the LAN. As another example, the control circuitry and the user device 310 can both connect to the Internet and communicate through the Internet. For example, the control circuitry can connect to the Internet through a WiFi router and the user device 310 can connect to the Internet through communication with a cellular communication system. As another example, the control circuitry can communicate directly with the user device 310 through a wireless communication protocol such as Bluetooth. As yet another example, the control circuitry can communicate with the user device 310 through a wireless communication protocol such as ZigBee, Z-Wave, or another wireless communication protocol suitable for the application. As another example, the control circuitry can communicate with the user device 310 through a wired connection such as, for example, a USB connector or another wired connection suitable for the application.

The user device 310 can display a variety of information and statistics related to sleep for the user 308 or user interaction with the bed 302 by the user 308. For example, a user interface displayed by the user device 310 can present information including amount of sleep for the user 308 over a period of time (e.g., a single evening, a week, a month, etc.) amount of deep sleep, ratio of deep sleep to restless sleep, time lapse between the user 308 getting into bed and the user 308 falling asleep, total amount of time spent in the bed 302 for a given period of time, heart rate for the user 308 over a period of time, respiration rate for the user 308 over a period of time, or other information related to user interaction with the bed 302 by the user 308 or one or more other users of the bed 302. In some implementations, information for multiple users can be presented on the user device 310, for example information for a first user positioned over the air chamber 306a can be presented along with information for a second user positioned over the air chamber 306b. In some implementations, the information presented on the user device 310 can vary according to the age of the user 308. For example, the information presented on the user device 310 can evolve with the age of the user 308 such that different information is presented on the user device 310 as the user 308 ages as a child or an adult.

The user device 310 can also be used as an interface for the control circuitry of the bed 302 to allow the user 308 to enter information. The information entered by the user 308 can be used by the control circuitry to provide better information to the user or to various control signals for controlling functions of the bed 302 or other devices. For example, the user can enter information such as weight, height, and age and the control circuitry can use this information to provide the user 308 with a comparison of the user's tracked sleep information to sleep information of other people having similar weights, heights, and/or ages as the user 308. As another example, the user 308 can use the user device 310 as an interface for controlling air pressure of the air chambers 306a and 306b, for controlling various recline or incline positions of the bed 302, for controlling temperature of one or more surface temperature control devices of the bed 302, or for allowing the control circuitry to generate control signals for other devices (as described in greater detail below).

In some implementations, control circuitry of the bed 302 (e.g., control circuitry integrated into the pump 304) can communicate with other devices or systems in addition to or instead of the user device 310. For example, the control circuitry can communicate with the television 312, a lighting system 314, a thermostat 316, a security system 318, or other house hold devices such as an oven 322, a coffee maker 324, a lamp 326, and a nightlight 328. Other examples of devices and/or systems that the control circuitry can communicate with include a system for controlling window blinds 330, one or more devices for detecting or controlling the states of one or more doors 332 (such as detecting if a door is open, detecting if a door is locked, or automatically locking a door), and a system for controlling a garage door 320 (e.g., control circuitry integrated with a garage door opener for identifying an open or closed state of the garage door 320 and for causing the garage door opener to open or close the garage door 320). Communications between the control circuitry of the bed 302 and other devices can occur through a network (e.g., a LAN or the Internet) or as point-to-point communication (e.g., using Bluetooth, radio communication, or a wired connection). In some implementations, control circuitry of different beds 302 can communicate with different sets of devices. For example, a kid bed may not communicate with and/or control the same devices as an adult bed. In some embodiments, the bed 302 can evolve with the age of the user such that the control circuitry of the bed 302 communicates with different devices as a function of age of the user.

The control circuitry can receive information and inputs from other devices/systems and use the received information and inputs to control actions of the bed 302 or other devices. For example, the control circuitry can receive information from the thermostat 316 indicating a current environmental temperature for a house or room in which the bed 302 is located. The control circuitry can use the received information (along with other information) to determine if a temperature of all or a portion of the surface of the bed 302 should be raised or lowered. The control circuitry can then cause a heating or cooling mechanism of the bed 302 to raise or lower the temperature of the surface of the bed 302. For example, the user 308 can indicate a desired sleeping temperature of 74 degrees while a second user of the bed 302 indicates a desired sleeping temperature of 72 degrees. The thermostat 316 can indicate to the control circuitry that the current temperature of the bedroom is 72 degrees. The control circuitry can identify that the user 308 has indicated a desired sleeping temperature of 74 degrees, and send control signals to a heating pad located on the user 308's side of the bed to raise the temperature of the portion of the surface of the bed 302 where the user 308 is located to raise the temperature of the user 308's sleeping surface to the desired temperature.

The control circuitry can also generate control signals controlling other devices and propagate the control signals to the other devices. In some implementations, the control signals are generated based on information collected by the control circuitry, including information related to user interaction with the bed 302 by the user 308 and/or one or more other users. In some implementations, information collected from one or more other devices other than the bed 302 are used when generating the control signals. For example, information relating to environmental occurrences (e.g., environmental temperature, environmental noise level, and environmental light level), time of day, time of year, day of the week, or other information can be used when generating control signals for various devices in communication with the control circuitry of the bed 302. For example, information on the time of day can be combined with information relating to movement and bed presence of the user 308 to generate control signals for the lighting system 314. In some implementations, rather than or in addition to providing control signals for one or more other devices, the control circuitry can provide collected information (e.g., information related to user movement, bed presence, sleep state, or biometric signals for the user 308) to one or more other devices to allow the one or more other devices to utilize the collected information when generating control signals. For example, control circuitry of the bed 302 can provide information relating to user interactions with the bed 302 by the user 308 to a central controller (not shown) that can use the provided information to generate control signals for various devices, including the bed 302.

Still referring to FIG. 3, the control circuitry of the bed 302 can generate control signals for controlling actions of other devices, and transmit the control signals to the other devices in response to information collected by the control circuitry, including bed presence of the user 308, sleep state of the user 308, and other factors. For example, control circuitry integrated with the pump 304 can detect an increase in pressure in the air chamber 306b and use this detected increase in air pressure to determine that the user 308 is present on the bed 302. In some implementations, the control circuitry can identify a heart rate or respiratory rate for the user 308 to identify that the increase in pressure is due to a person sitting, laying, or otherwise resting on the bed 302 rather than an inanimate object (such as a suitcase) having been placed on the bed 302. In some implementations, the information indicating user bed presence is combined with other information to identify a current or future likely state for the user 308. For example, a detected user bed presence at 11:00 am may indicate that the user is sitting on the bed (e.g., to tie her shoes, or to read a book) and does not intend to go to sleep, while a detected user bed presence at 10:00 pm can indicate that the user 308 is in bed for the evening and is intending to fall asleep soon. As another example, if the control circuitry detects that the user 308 has left the bed 302 at 6:30 am (e.g., indicating that the user 308 has woken up for the day), and then later detects user bed presence of the user 308 at 7:30 am, the control circuitry can use this information that the newly detected user bed presence is likely temporary (e.g., while the user 308 ties her shoes before heading to work) rather than an indication that the user 308 is intending to stay on the bed 302 for an extended period.

In some implementations, the control circuitry is able to use collected information (including information related to user interaction with the bed 302 by the user 308, as well as environmental information, time information, and input received from the user) to identify use patterns for the user 308. For example, the control circuitry can use information indicating bed presence and sleep states for the user 308 collected over a period of time to identify a sleep pattern for the user. For example, the control circuitry can identify that the user 308 generally goes to bed between 9:30 pm and 10:00 pm, generally falls asleep between 10:00 pm and 11:00 pm, and generally wakes up between 6:30 am and 6:45 am based on information indicating user presence and biometrics for the user 308 collected over a week. The control circuitry can use identified patterns for a user to better process and identify user interactions with the bed 302 by the user 308. For example, given the above example user bed presence, sleep, and wake patterns for the user 308, if the user 308 is detected as being on the bed at 3:00 pm, the control circuitry can determine that the user's presence on the bed is only temporary, and use this determination to generate different control signals than would be generated if the control circuitry determined that the user 308 was in bed for the evening. As another example, if the control circuitry detects that the user 308 has gotten out of bed at 3:00 am, the control circuitry can use identified patterns for the user 308 to determine that the user has only gotten up temporarily (for example, to use the rest room, or get a glass of water) and is not up for the day. By contrast, if the control circuitry identifies that the user 308 has gotten out of the bed 302 at 6:40 am, the control circuitry can determine that the user is up for the day and generate a different set of control signals than those that would be generated if it were determined that the user 308 were only getting out of bed temporarily (as would be the case when the user 308 gets out of the bed 302 at 3:00 am). For other users 308, getting out of the bed 302 at 3:00 am may be the normal wake-up time, which the control circuitry can learn and respond to accordingly.

As described above, the control circuitry for the bed 302 can generate control signals for control functions of various other devices. The control signals can be generated, at least in part, based on detected interactions by the user 308 with the bed 302, as well as other information including time, date, temperature, etc. For example, the control circuitry can communicate with the television 312, receive information from the television 312, and generate control signals for controlling functions of the television 312. For example, the control circuitry can receive an indication from the television 312 that the television 312 is currently on. If the television 312 is located in a different room from the bed 302, the control circuitry can generate a control signal to turn the television 312 off upon making a determination that the user 308 has gone to bed for the evening. For example, if bed presence of the user 308 in the bed 302 is detected during a particular time range (e.g., between 8:00 pm and 7:00 am) and persists for longer than a threshold period of time (e.g., 10 minutes) the control circuitry can use this information to determine that the user 308 is in bed for the evening. If the television 312 is on (as indicated by communications received by the control circuitry of the bed 302 from the television 312) the control circuitry can generate a control signal to turn the television 312 off. The control signals can then be transmitted to the television (e.g., through a directed communication link between the television 312 and the control circuitry or through a network). As another example, rather than turning off the television 312 in response to detection of user bed presence, the control circuitry can generate a control signal that causes the volume of the television 312 to be lowered by a pre-specified amount.

As another example, upon detecting that the user 308 has left the bed 302 during a specified time range (e.g., between 6:00 am and 8:00 am) the control circuitry can generate control signals to cause the television 312 to turn on and tune to a pre-specified channel (e.g., the user 308 has indicated a preference for watching the morning news upon getting out of bed in the morning). The control circuitry can generate the control signal and transmit the signal to the television 312 to cause the television 312 to turn on and tune to the desired station (which could be stored at the control circuitry, the television 312, or another location). As another example, upon detecting that the user 308 has gotten up for the day, the control circuitry can generate and transmit control signals to cause the television 312 to turn on and begin playing a previously recorded program from a digital video recorder (DVR) in communication with the television 312.

As another example, if the television 312 is in the same room as the bed 302, the control circuitry does not cause the television 312 to turn off in response to detection of user bed presence. Rather, the control circuitry can generate and transmit control signals to cause the television 312 to turn off in response to determining that the user 308 is asleep. For example, the control circuitry can monitor biometric signals of the user 308 (e.g., motion, heart rate, respiration rate) to determine that the user 308 has fallen asleep. Upon detecting that the user 308 is sleeping, the control circuitry generates and transmits a control signal to turn the television 312 off. As another example, the control circuitry can generate the control signal to turn off the television 312 after a threshold period of time after the user 308 has fallen asleep (e.g., 10 minutes after the user has fallen asleep). As another example, the control circuitry generates control signals to lower the volume of the television 312 after determining that the user 308 is asleep. As yet another example, the control circuitry generates and transmits a control signal to cause the television to gradually lower in volume over a period of time and then turn off in response to determining that the user 308 is asleep.

In some implementations, the control circuitry can similarly interact with other media devices, such as computers, tablets, smart phones, stereo systems, etc. For example, upon detecting that the user 308 is asleep, the control circuitry can generate and transmit a control signal to the user device 310 to cause the user device 310 to turn off, or turn down the volume on a video or audio file being played by the user device 310.

The control circuitry can additionally communicate with the lighting system 314, receive information from the lighting system 314, and generate control signals for controlling functions of the lighting system 314. For example, upon detecting user bed presence in the bed 302 during a certain time frame (e.g., between 8:00 pm and 7:00 am) that lasts for longer than a threshold period of time (e.g., 10 minutes) the control circuitry of the bed 302 can determine that the user 308 is in bed for the evening. In response to this determination, the control circuitry can generate control signals to cause lights in one or more rooms other than the room in which the bed 302 is located to switch off. The control signals can then be transmitted to the lighting system 314 and executed by the lighting system 314 to cause the lights in the indicated rooms to shut off. For example, the control circuitry can generate and transmit control signals to turn off lights in all common rooms, but not in other bedrooms. As another example, the control signals generated by the control circuitry can indicate that lights in all rooms other than the room in which the bed 302 is located are to be turned off, while one or more lights located outside of the house containing the bed 302 are to be turned on, in response to determining that the user 308 is in bed for the evening. Additionally, the control circuitry can generate and transmit control signals to cause the nightlight 328 to turn on in response to determining user 308 bed presence or whether the user 308 is asleep. As another example, the control circuitry can generate first control signals for turning off a first set of lights (e.g., lights in common rooms) in response to detecting user bed presence, and second control signals for turning off a second set of lights (e.g., lights in the room in which the bed 302 is located) in response to detecting that the user 308 is asleep.

In some implementations, in response to determining that the user 308 is in bed for the evening, the control circuitry of the bed 302 can generate control signals to cause the lighting system 314 to implement a sunset lighting scheme in the room in which the bed 302 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 308 to sleep, and therefore is logically implemented when the control circuitry has determined that the user 308 is in bed for the evening.

The control circuitry can also be configured to implement a sunrise lighting scheme when the user 308 wakes up in the morning. The control circuitry can determine that the user 308 is awake for the day, for example, by detecting that the user 308 has gotten off of the bed 302 (i.e., is no longer present on the bed 302) during a specified time frame (e.g., between 6:00 am and 9:00 am). As another example, the control circuitry can monitor movement, heart rate, respiratory rate, or other biometric signals of the user 308 to determine that the user 308 is awake even though the user 308 has not gotten out of bed. If the control circuitry detects that the user is awake during a specified time frame, the control circuitry can determine that the user 308 is awake for the day. The specified time frame can be, for example, based on previously recorded user bed presence information collected over a period of time (e.g., two weeks) that indicates that the user 308 usually wakes up for the day between 6:30 am and 7:30 am. In response to the control circuitry determining that the user 308 is awake, the control circuitry can generate control signals to cause the lighting system 314 to implement the sunrise lighting scheme in the bedroom in which the bed 302 is located. The sunrise lighting scheme can include, for example, turning on lights (e.g., the lamp 326, or other lights in the bedroom). The sunrise lighting scheme can further include gradually increasing the level of light in the room where the bed 302 is located (or in one or more other rooms). The sunrise lighting scheme can also include only turning on lights of specified colors. For example, the sunrise lighting scheme can include lighting the bedroom with blue light to gently assist the user 308 in waking up and becoming active.

In some implementations, the control circuitry can generate different control signals for controlling actions of the lighting system 314 depending on a time of day that user interactions with the bed 302 are detected. For example, the control circuitry can use historical user interaction information for interactions between the user 308 and the bed 302 to determine that the user 308 usually falls asleep between 10:00 pm and 11:00 pm and usually wakes up between 6:30 am and 7:30 am on weekdays. The control circuitry can use this information to generate a first set of control signals for controlling the lighting system 314 if the user 308 is detected as getting out of bed at 3:00 am and to generate a second set of control signals for controlling the lighting system 314 if the user 308 is detected as getting out of bed after 6:30 am. For example, if the user 308 gets out of bed prior to 6:30 am, the control circuitry can turn on lights that guide the user 308's route to a restroom. As another example, if the user 308 gets out of bed prior to 6:30 am, the control circuitry can turn on lights that guide the user 308's route to the kitchen (which can include, for example, turning on the nightlight 328, turning on under bed lighting, or turning on the lamp 326).

As another example, if the user 308 gets out of bed after 6:30 am, the control circuitry can generate control signals to cause the lighting system 314 to initiate a sunrise lighting scheme, or to turn on one or more lights in the bedroom and/or other rooms. In some implementations, if the user 308 is detected as getting out of bed prior to a specified morning rise time for the user 308, the control circuitry causes the lighting system 314 to turn on lights that are dimmer than lights that are turned on by the lighting system 314 if the user 308 is detected as getting out of bed after the specified morning rise time. Causing the lighting system 314 to only turn on dim lights when the user 308 gets out of bed during the night (i.e., prior to normal rise time for the user 308) can prevent other occupants of the house from being woken by the lights while still allowing the user 308 to see in order to reach the restroom, kitchen, or another destination within the house.

The historical user interaction information for interactions between the user 308 and the bed 302 can be used to identify user sleep and awake time frames. For example, user bed presence times and sleep times can be determined for a set period of time (e.g., two weeks, a month, etc.). The control circuitry can then identify a typical time frame in which the user 308 goes to bed, a typical time frame for when the user 308 falls asleep, and a typical time frame for when the user 308 wakes up (and in some cases, different time frames for when the user 308 wakes up and when the user 308 actually gets out of bed). In some implementations, buffer time can be added to these time frames. For example, if the user is identified as typically going to bed between 10:00 pm and 10:30 pm, a buffer of a half hour in each direction can be added to the time frame such that any detection of the user getting onto the bed between 9:30 pm and 11:00 pm is interpreted as the user 308 going to bed for the evening. As another example, detection of bed presence of the user starting from a half hour before the earliest typical time that the user 308 goes to bed extending until the typical wake up time (e.g., 6:30 am) for the user can be interpreted as the user going to bed for the evening. For example, if the user typically goes to bed between 10:00 pm and 10:30 pm, if the user's bed presence is sensed at 12:30 am one night, that can be interpreted as the user getting into bed for the evening even though this is outside of the user's typical time frame for going to bed because it has occurred prior to the user's normal wake up time. In some implementations, different time frames are identified for different times of the year (e.g., earlier bed time during winter vs. summer) or at different times of the week (e.g., user wakes up earlier on weekdays than on weekends).

The control circuitry can additionally communicate with the thermostat 316, receive information from the thermostat 316, and generate control signals for controlling functions of the thermostat 316. For example, the user 308 can indicate user preferences for different temperatures at different times, depending on the sleep state or bed presence of the user 308. For example, the user 308 may prefer an environmental temperature of 72 degrees when out of bed, 70 degrees when in bed but awake, and 68 degrees when sleeping. The control circuitry of the bed 302 can detect bed presence of the user 308 in the evening and determine that the user 308 is in bed for the night. In response to this determination, the control circuitry can generate control signals to cause the thermostat to change the temperature to 70 degrees. The control circuitry can then transmit the control signals to the thermostat 316. Upon detecting that the user 308 is asleep, the control circuitry can generate and transmit control signals to cause the thermostat 316 to change the temperature to 68. The next morning, upon determining that the user is awake for the day (e.g., the user 308 gets out of bed after 6:30 am) the control circuitry can generate and transmit control circuitry to cause the thermostat to change the temperature to 72 degrees.

In some implementations, the control circuitry can similarly generate control signals to cause one or more heating or cooling elements on the surface of the bed 302 to change temperature at various times, either in response to user interaction with the bed 302 or at various pre-programmed times. For example, the control circuitry can activate a heating element to raise the temperature of one side of the surface of the bed 302 to 73 degrees when it is detected that the user 308 has fallen asleep. As another example, upon determining that the user 308 is up for the day, the control circuitry can turn off a heating or cooling element. As yet another example, the user 308 can pre-program various times at which the temperature at the surface of the bed should be raised or lowered. For example, the user can program the bed 302 to raise the surface temperature to 76 degrees at 10:00 pm, and lower the surface temperature to 68 degrees at 11:30 pm.

In some implementations, in response to detecting user bed presence of the user 308 and/or that the user 308 is asleep, the control circuitry can cause the thermostat 316 to change the temperature in different rooms to different values. For example, in response to determining that the user 308 is in bed for the evening, the control circuitry can generate and transmit control signals to cause the thermostat 316 to set the temperature in one or more bedrooms of the house to 72 degrees and set the temperature in other rooms to 67 degrees.

The control circuitry can also receive temperature information from the thermostat 316 and use this temperature information to control functions of the bed 302 or other devices. For example, as discussed above, the control circuitry can adjust temperatures of heating elements included in the bed 302 in response to temperature information received from the thermostat 316.

In some implementations, the control circuitry can generate and transmit control signals for controlling other temperature control systems. For example, in response to determining that the user 308 is awake for the day, the control circuitry can generate and transmit control signals for causing floor heating elements to activate. For example, the control circuitry can cause a floor heating system for a master bedroom to turn on in response to determining that the user 308 is awake for the day.

The control circuitry can additionally communicate with the security system 318, receive information from the security system 318, and generate control signals for controlling functions of the security system 318. For example, in response to detecting that the user 308 in is bed for the evening, the control circuitry can generate control signals to cause the security system to engage security functions. The control circuitry can then transmit the control signals to the security system 318 to cause the security system 318 to engage. As another example, the control circuitry can generate and transmit control signals to cause the security system 318 to disable in response to determining that the user 308 is awake for the day (e.g., user 308 is no longer present in the bed 302 after 6:00 am). In some implementations, the control circuitry can generate and transmit a first set of control signals to cause the security system 318 to engage a first set of security features in response to detecting user bed presence of the user 308, and can generate and transmit a second set of control signals to cause the security system 318 to engage a second set of security features in response to detecting that the user 308 has fallen asleep.

In some implementations, the control circuitry can receive alerts from the security system 318 and indicate the alert to the user 308. For example, the control circuitry can detect that the user 308 is in bed for the evening and in response, generate and transmit control signals to cause the security system 318 to engage. The security system can then detect a security breach (e.g., someone has opened the door 332 without entering the security code, or someone has opened a window when the security system 318 is engaged). The security system 318 can communicate the security breach to the control circuitry of the bed 302. In response to receiving the communication from the security system 318, the control circuitry can generate control signals to alert the user 308 to the security breach. For example, the control circuitry can cause the bed 302 to vibrate. As another example, the control circuitry can cause portions of the bed 302 to articulate (e.g., cause the head section to raise or lower) in order to wake the user 308 and alert the user to the security breach. As another example, the control circuitry can generate and transmit control signals to cause the lamp 326 to flash on and off at regular intervals to alert the user 308 to the security breach. As another example, the control circuitry can alert the user 308 of one bed 302 regarding a security breach in a bedroom of another bed, such as an open window in a kid's bedroom.

The control circuitry can additionally generate and transmit control signals for controlling the garage door 320 and receive information indicating a state of the garage door 320 (i.e., open or closed). For example, in response to determining that the user 308 is in bed for the evening, the control circuitry can generate and transmit a request to a garage door opener or another device capable of sensing if the garage door 320 is open. The request can request information on the current state of the garage door 320. If the control circuitry receives a response (e.g., from the garage door opener) indicating that the garage door 320 is open, the control circuitry can either notify the user 308 that the garage door is open, or generate a control signal to cause the garage door opener to close the garage door 320. For example, the control circuitry can send a message to the user device 310 indicating that the garage door is open. As another example, the control circuitry can cause the bed 302 to vibrate. As yet another example, the control circuitry can generate and transmit a control signal to cause the lighting system 314 to cause one or more lights in the bedroom to flash to alert the user 308 to check the user device 310 for an alert (in this example, an alert regarding the garage door 320 being open). Alternatively, or additionally, the control circuitry can generate and transmit control signals to cause the garage door opener to close the garage door 320 in response to identifying that the user 308 is in bed for the evening and that the garage door 320 is open. In some implementations, control signals can vary depend on the age of the user 308.

The control circuitry can similarly send and receive communications for controlling or receiving state information associated with the door 332 or the oven 322. For example, upon detecting that the user 308 is in bed for the evening, the control circuitry can generate and transmit a request to a device or system for detecting a state of the door 332. Information returned in response to the request can indicate various states for the door 332 such as open, closed but unlocked, or closed and locked. If the door 332 is open or closed but unlocked, the control circuitry can alert the user 308 to the state of the door, such as in a manner described above with reference to the garage door 320. Alternatively, or in addition to alerting the user 308, the control circuitry can generate and transmit control signals to cause the door 332 to lock, or to close and lock. If the door 332 is closed and locked, the control circuitry can determine that no further action is needed.

Similarly, upon detecting that the user 308 is in bed for the evening, the control circuitry can generate and transmit a request to the oven 322 to request a state of the oven 322 (e.g., on or off). If the oven 322 is on, the control circuitry can alert the user 308 and/or generate and transmit control signals to cause the oven 322 to turn off. If the oven is already off, the control circuitry can determine that no further action is necessary. In some implementations, different alerts can be generated for different events. For example, the control circuitry can cause the lamp 326 (or one or more other lights, via the lighting system 314) to flash in a first pattern if the security system 318 has detected a breach, flash in a second pattern if garage door 320 is on, flash in a third pattern if the door 332 is open, flash in a fourth pattern if the oven 322 is on, and flash in a fifth pattern if another bed has detected that a user of that bed has gotten up (e.g., that a child of the user 308 has gotten out of bed in the middle of the night as sensed by a sensor in the bed 302 of the child). Other examples of alerts that can be processed by the control circuitry of the bed 302 and communicated to the user include a smoke detector detecting smoke (and communicating this detection of smoke to the control circuitry), a carbon monoxide tester detecting carbon monoxide, a heater malfunctioning, or an alert from any other device capable of communicating with the control circuitry and detecting an occurrence that should be brought to the user 308's attention.

The control circuitry can also communicate with a system or device for controlling a state of the window blinds 330. For example, in response to determining that the user 308 is in bed for the evening, the control circuitry can generate and transmit control signals to cause the window blinds 330 to close. As another example, in response to determining that the user 308 is up for the day (e.g., user has gotten out of bed after 6:30 am) the control circuitry can generate and transmit control signals to cause the window blinds 330 to open. By contrast, if the user 308 gets out of bed prior to a normal rise time for the user 308, the control circuitry can determine that the user 308 is not awake for the day and does not generate control signals for causing the window blinds 330 to open. As yet another example, the control circuitry can generate and transmit control signals that cause a first set of blinds to close in response to detecting user bed presence of the user 308 and a second set of blinds to close in response to detecting that the user 308 is asleep.

The control circuitry can generate and transmit control signals for controlling functions of other household devices in response to detecting user interactions with the bed 302. For example, in response to determining that the user 308 is awake for the day, the control circuitry can generate and transmit control signals to the coffee maker 324 to cause the coffee maker 324 to begin brewing coffee. As another example, the control circuitry can generate and transmit control signals to the oven 322 to cause the oven to begin preheating (for users that like fresh baked bread in the morning). As another example, the control circuitry can use information indicating that the user 308 is awake for the day along with information indicating that the time of year is currently winter and/or that the outside temperature is below a threshold value to generate and transmit control signals to cause a car engine block heater to turn on.

As another example, the control circuitry can generate and transmit control signals to cause one or more devices to enter a sleep mode in response to detecting user bed presence of the user 308, or in response to detecting that the user 308 is asleep. For example, the control circuitry can generate control signals to cause a mobile phone of the user 308 to switch into sleep mode. The control circuitry can then transmit the control signals to the mobile phone. Later, upon determining that the user 308 is up for the day, the control circuitry can generate and transmit control signals to cause the mobile phone to switch out of sleep mode.

In some implementations, the control circuitry can communicate with one or more noise control devices. For example, upon determining that the user 308 is in bed for the evening, or that the user 308 is asleep, the control circuitry can generate and transmit control signals to cause one or more noise cancellation devices to activate. The noise cancellation devices can, for example, be included as part of the bed 302 or located in the bedroom with the bed 302. As another example, upon determining that the user 308 is in bed for the evening or that the user 308 is asleep, the control circuitry can generate and transmit control signals to turn the volume on, off, up, or down, for one or more sound generating devices, such as a stereo system radio, computer, tablet, etc.

Additionally, functions of the bed 302 are controlled by the control circuitry in response to user interactions with the bed 302. For example, the bed 302 can include an adjustable foundation and an articulation controller configured to adjust the position of one or more portions of the bed 302 by adjusting the adjustable foundation that supports the bed. For example, the articulation controller can adjust the bed 302 from a flat position to a position in which a head portion of a mattress of the bed 302 is inclined upward (e.g., to facilitate a user sitting up in bed and/or watching television). In some implementations, the bed 302 includes multiple separately articulable sections. For example, portions of the bed corresponding to the locations of the chambers 306a and 306b can be articulated independently from each other, to allow one person positioned on the bed 302 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 302 may include more than one zone that can be independently adjusted. The articulation controller may also be configured to provide different levels of massage to one or more users on the bed 302 or to cause the bed to vibrate to communicate alerts to the user 308 as described above.

The control circuitry can adjust positions (e.g., incline and decline positions for the user 308 and/or an additional user of the bed 302) in response to user interactions with the bed 302. For example, the control circuitry can cause the articulation controller to adjust the bed 302 to a first recline position for the user 308 in response to sensing user bed presence for the user 308. The control circuitry can cause the articulation controller to adjust the bed 302 to a second recline position (e.g., a less reclined, or flat position) in response to determining that the user 308 is asleep. As another example, the control circuitry can receive a communication from the television 312 indicating that the user 308 has turned off the television 312, and in response the control circuitry can cause the articulation controller to adjust the position of the bed 302 to a preferred user sleeping position (e.g., due to the user turning off the television 312 while the user 308 is in bed indicating that the user 308 wishes to go to sleep).

In some implementations, the control circuitry can control the articulation controller so as to wake up one user of the bed 302 without waking another user of the bed 302. For example, the user 308 and a second user of the bed 302 can each set distinct wakeup times (e.g., 6:30 am and 7:15 am respectively). When the wakeup time for the user 308 is reached, the control circuitry can cause the articulation controller to vibrate or change the position of only a side of the bed on which the user 308 is located to wake the user 308 without disturbing the second user. When the wakeup time for the second user is reached, the control circuitry can cause the articulation controller to vibrate or change the position of only the side of the bed on which the second user is located. Alternatively, when the second wakeup time occurs, the control circuitry can utilize other methods (such as audio alarms, or turning on of lights) to wake the second user since the user 308 is already awake and therefore will not be disturbed when the control circuitry attempts to wake the second user.

Still referring to FIG. 3, the control circuitry for the bed 302 can utilize information for interactions with the bed 302 by multiple users to generate control signals for controlling functions of various other devices. For example, the control circuitry can wait to generate control signals for, for example, engaging the security system 318, or instructing the lighting system 314 to turn off lights in various rooms until both the user 308 and a second user are detected as being present on the bed 302. As another example, the control circuitry can generate a first set of control signals to cause the lighting system 314 to turn off a first set of lights upon detecting bed presence of the user 308 and generate a second set of control signals for turning off a second set of lights in response to detecting bed presence of a second user. As another example, the control circuitry can wait until it has been determined that both the user 308 and a second user are awake for the day before generating control signals to open the window blinds 330. As yet another example, in response to determining that the user 308 has left the bed and is awake for the day, but that a second user is still sleeping, the control circuitry can generate and transmit a first set of control signals to cause the coffee maker 324 to begin brewing coffee, to cause the security system 318 to deactivate, to turn on the lamp 326, to turn off the nightlight 328, to cause the thermostat 316 to raise the temperature in one or more rooms to 72 degrees, and to open blinds (e.g., the window blinds 330) in rooms other than the bedroom. Later, in response to detecting that the second user is no longer present in the bed (or that the second user is awake) the control circuitry can generate and transmit a second set of control signals to, for example, cause the lighting system 314 to turn on one or more lights in the bedroom, to cause window blinds in the bedroom to open, and to turn on the television 312 to a pre-specified channel.

Figure 4A:
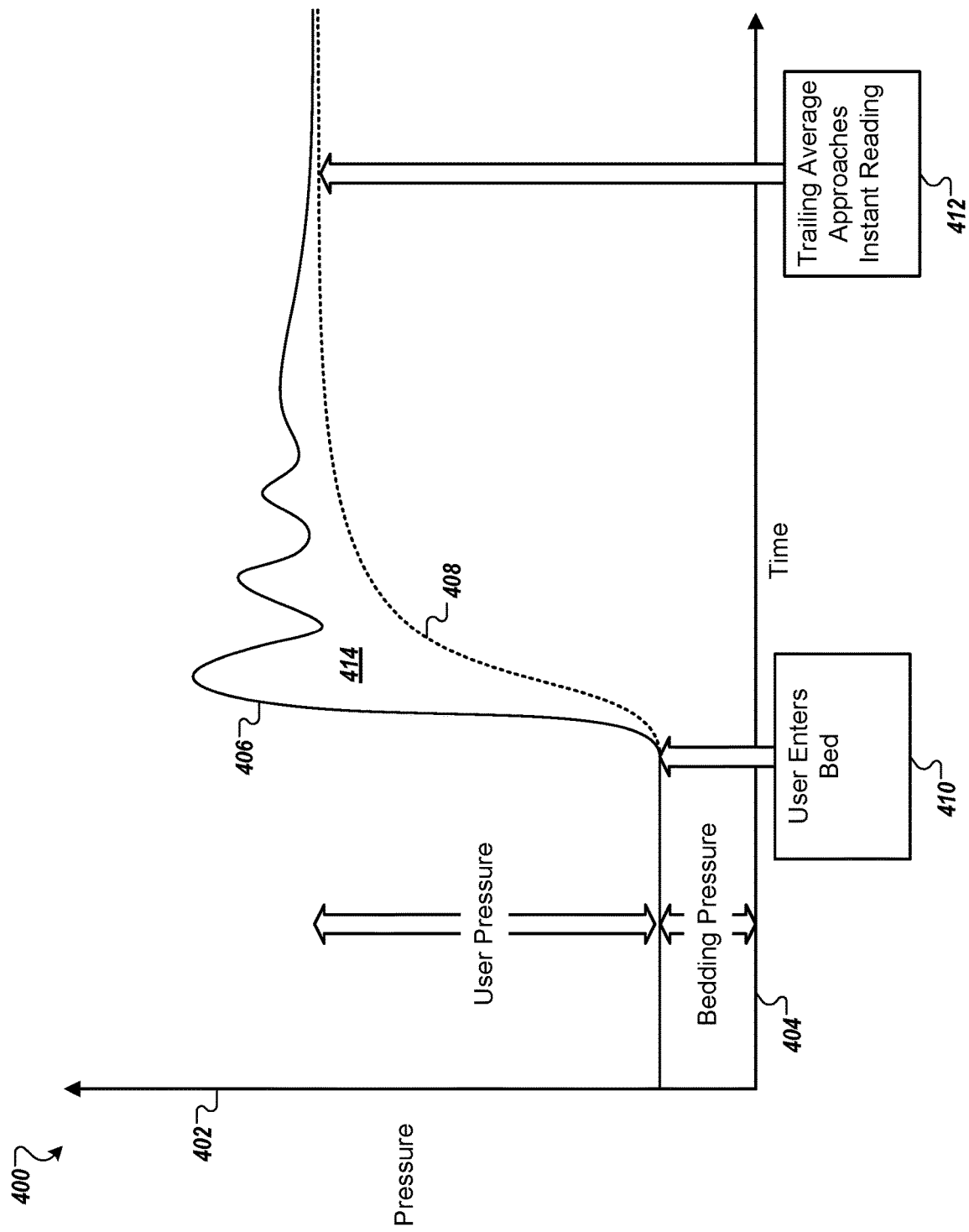
FIGS. 4A and 4B are graphs showing instant pressure readings and trailing averages that may be used to detect user presence in a bed.
Figure 4B:
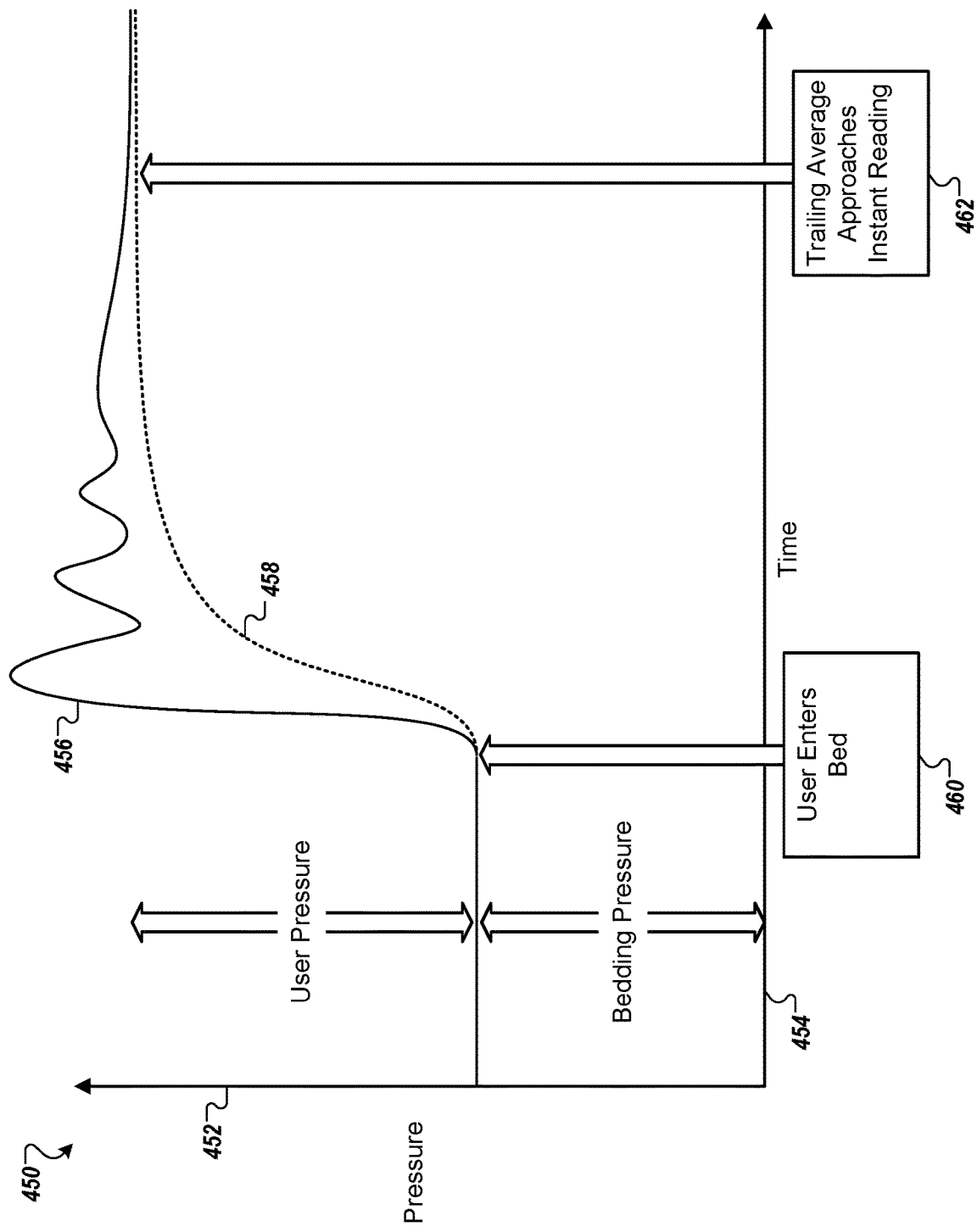

FIGS. 4A and 4B are graphs 400 and 450 showing instant pressure readings and trailing averages that may be used to detect user presence in a bed. The vertical axes 402 and 452 represent pressure, such as may be measured by the pump 304, and the horizontal axes 404 and 454 represent time, such as may be measured by the control circuitry discussed with respect to FIG. 3 above. The graphs 400 and 450 show the instant pressure readings over time with curves 406 and 456. Curves 408 and 458 shows a trailing average of the instant pressure readings, for example as calculated by the control circuitry.

In graph 400, at the beginning of the time series, the bed is not occupied by a user. The bed's instant pressure reading is a positive value that is influenced, for example, by how firm the bed's mattress is inflated, and the weight of bedding or other material on the mattress. In this example, the mattress is being measured in the summer, when a user is likely to have less bedding on the bed than in the winter. With no changes to the bed's firmness or load, the instant pressure reading curve 406 remains flat, indicating a generally constant pressure, until the a user entrance event 410.

The user entrance event 410 represents a user entering the bed. When the user enters the bed, the instant pressure reading curve 406 shows a sharp spike in pressure, followed by some oscillation around some, possibly unknown, final pressure value. This sharp spike and oscillation may be caused, at least in part, by the fluid mechanics of the air inside the air bladder(s) of the mattress, the movement of the user as they enter the bed, and noise in the pressure sensor in the pump 304, as well as other sources. However, after the user enters the bed, they often stay relatively still, for example to sleep, watch television, use a computing device, or read. As the user reduces their movement, and as the fluid mechanics of air bladder approach equilibrium, the oscillation in the instant pressure reading curve 406 will often reduce. Over time, the instant pressure reading curve 406 may either approach or reach a new constant pressure that is caused by the weight of the user in addition to how firm the bed's mattress is inflated, and the weight of bedding or other material on the mattress.

One process for determining when this new constant pressure is reached involves the use of the trailing average curve 408. As the instant pressure reading curve 406 approaches or meets the trailing average curve 408 in event 412, a computer system such as the logic circuitry may determine that the bed is occupied by a user.

The trailing average curve 408 represents an average value calculated from N previous instant pressure readings shown in the instant pressure reading curve 406. For example, for an N value of 4, and four previous instant pressure readings of 1023, 1145, 0977, and 1002, the trailing average value would be 1036.75, possibly rounded to 1037. When plotted on the graph 400, the instant pressure reading curve 406 would be plotted at 1002, the final of the N values and the trailing average curve 408 would be plotted at 1037 at the same time value (e.g., the same location along the horizontal axis 404).

The particular calculation used for the trailing average can be selected based on, for example, the configuration of the mattress, pump, sensors, and users involved. For example, the trailing average may be weighted to favor more recent instant pressure readings, and the value for N may be greater than or less than 5 and may be static or dynamic. Outlier values within the trailing average may be removed. A sample rate lower than the sample rate of instant pressure readings may be used. Missing values (e.g., due to hardware or network errors) may be interpolated from surrounding values or treated as outliers.

As previously described, one test for occupancy of the bed can include determining that the instant pressure reading curve 406 and the trailing average curve 408 approach each other (e.g., either crossing or coming within a threshold value of each other). However, the graph 400 may be used for other occupancy tests. For example, an area between the curves 414 may be tracked, and once the area 414 is of sufficient size, a computer device may determine that the bed is occupied. In another example, the oscillation of the instant pressure reading curve 406 may be compared to the oscillation of the trailing average curve 408, and once their oscillations are within a threshold similarity, a computer device may determine that the bed is occupied.

FIG. 4B shows a similar graph 450 to the graph 400. In this graph 450, the initial instant pressure reading curve 458 is shown with a higher pressure than in the graph 400. This increase in initial pressure may be from, for example, using a different air bladder, inflating the air bladder to a greater firmness, or adding additional bedding to the mattress. For example, the graph 400 may represent some bed in the summer, and the graph 450 may represent the same bed in the winter, when the user has heavier bedding on the bed to account for colder temperatures.

As can be seen by comparing the graphs 400 and 450, with other values held constant, this initial pressure value does not affect the identification of the events 412 and 462 for determining that the bed is occupied. As such, the use of a trailing average compared to instant pressure readings may be used for bed occupancy determination without the need to control for the amount or type of bedding on the bed.

Figure 5:
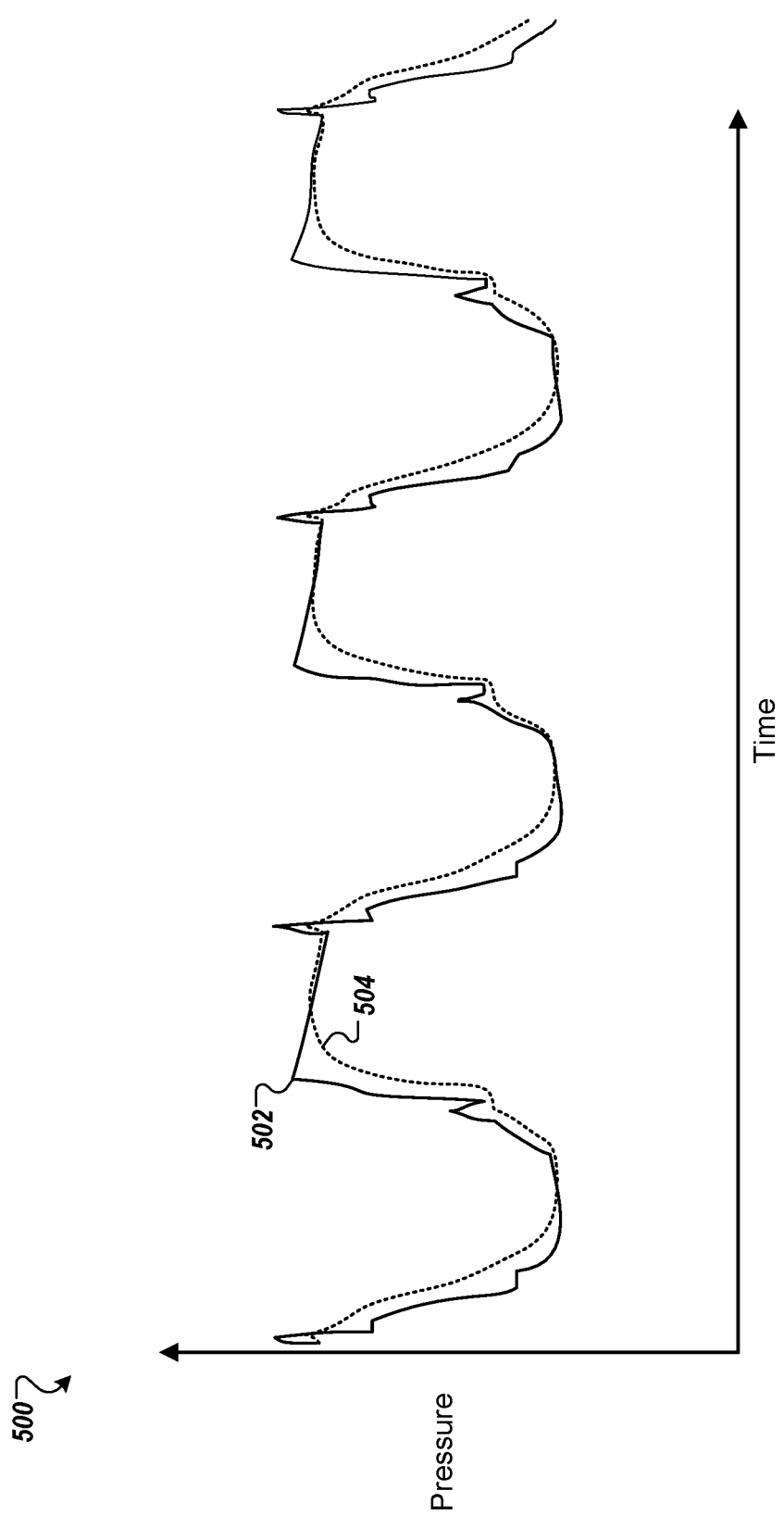
FIG. 5 is a graph showing instant and smoothed pressure readings from a bed.

FIG. 5 is a graph 500 showing instant 502 and smoothed 504 pressure readings from a bed. The vertical axis 506 represents pressure, such as may be measured by the control circuitry discussed with respect to FIG. 3 above. The graph 500 shows the instant pressure reading over time with curve 502 and curve 504 shows a smoothed pressure reading, for example as calculated by the control circuitry.

Unlike the instant pressure readings in the graphs 400 and 450, the instant pressure readings 502 do not oscillate after an initial spike when a user enters the bed. Instead, there is an initial spike when the user enters the bed, followed by a slow reduction in pressure as the fluid dynamic forces in the bed approach equilibrium. When the user exits the bed, there is another, smaller spike, followed by a swift reduction in pressure.

To generate the smoothed curve 504, a computer device such as the control circuits can apply any appropriate line smoothing technique. One such line smoothing algorithm includes averaging a particular reading with N earlier and M later instant pressure readings. For example, if N=1 and M=2, and for a reading of 741 preceded by preceded by 134 and followed by 740 and 735, the smoothed curve can have a value at the same time of 587.5, possibly rounded to 587, as calculated by a computer device such as the control circuitry. In some cases, M or N may be of value 0. Other smoothing functions, or combinations of functions, may be used.

As will be described with respect to FIGS. 6 and 7 below, one or both of the curves 502 and 504 may be used by a computing device such as the control circuitry in determining user presence in a bed.

Figure 6:
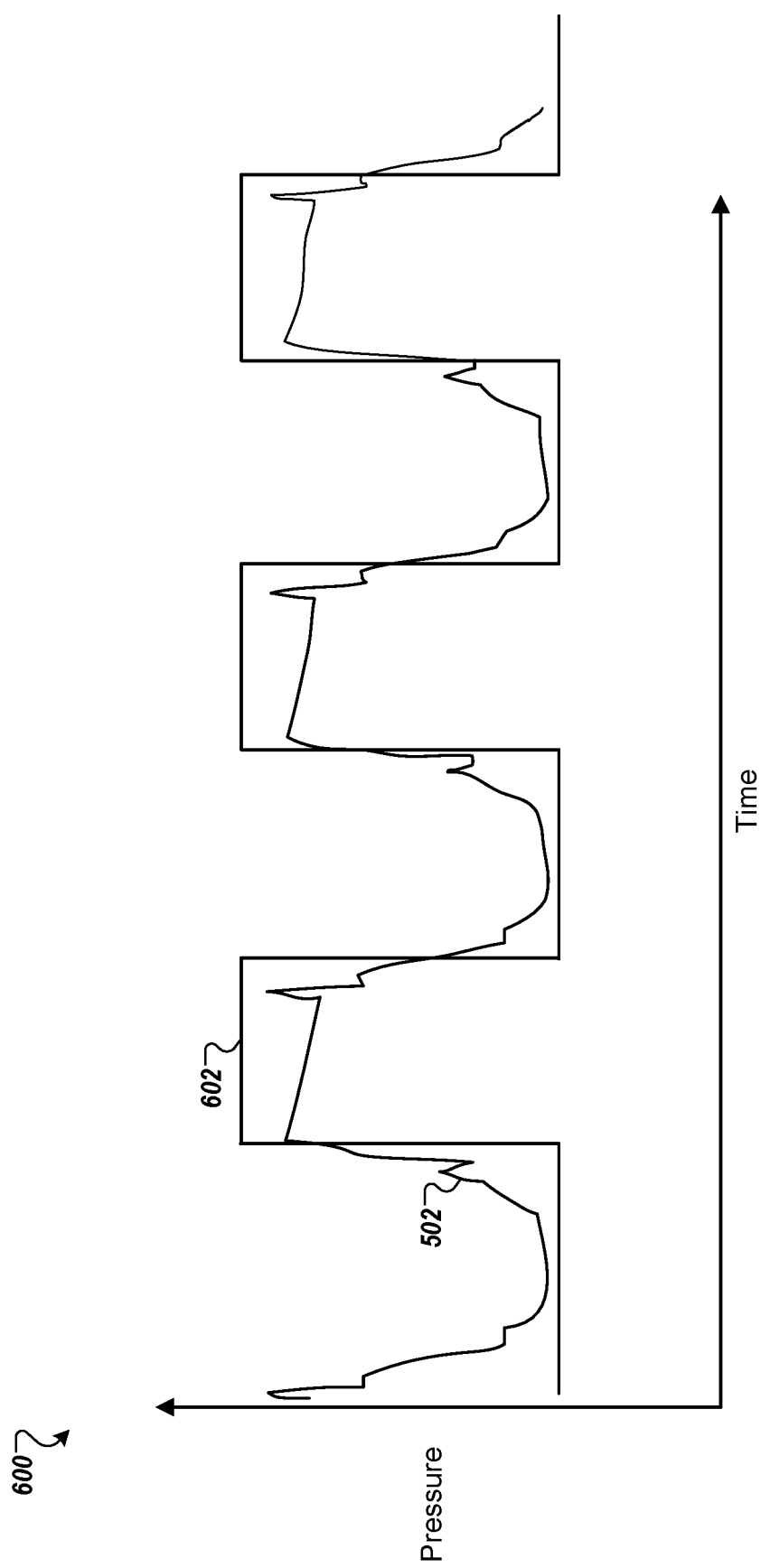
FIG. 6 is a graph showing instant pressure readings compared to a threshold that may be used to detect user presence in a bed.
Figure 7:
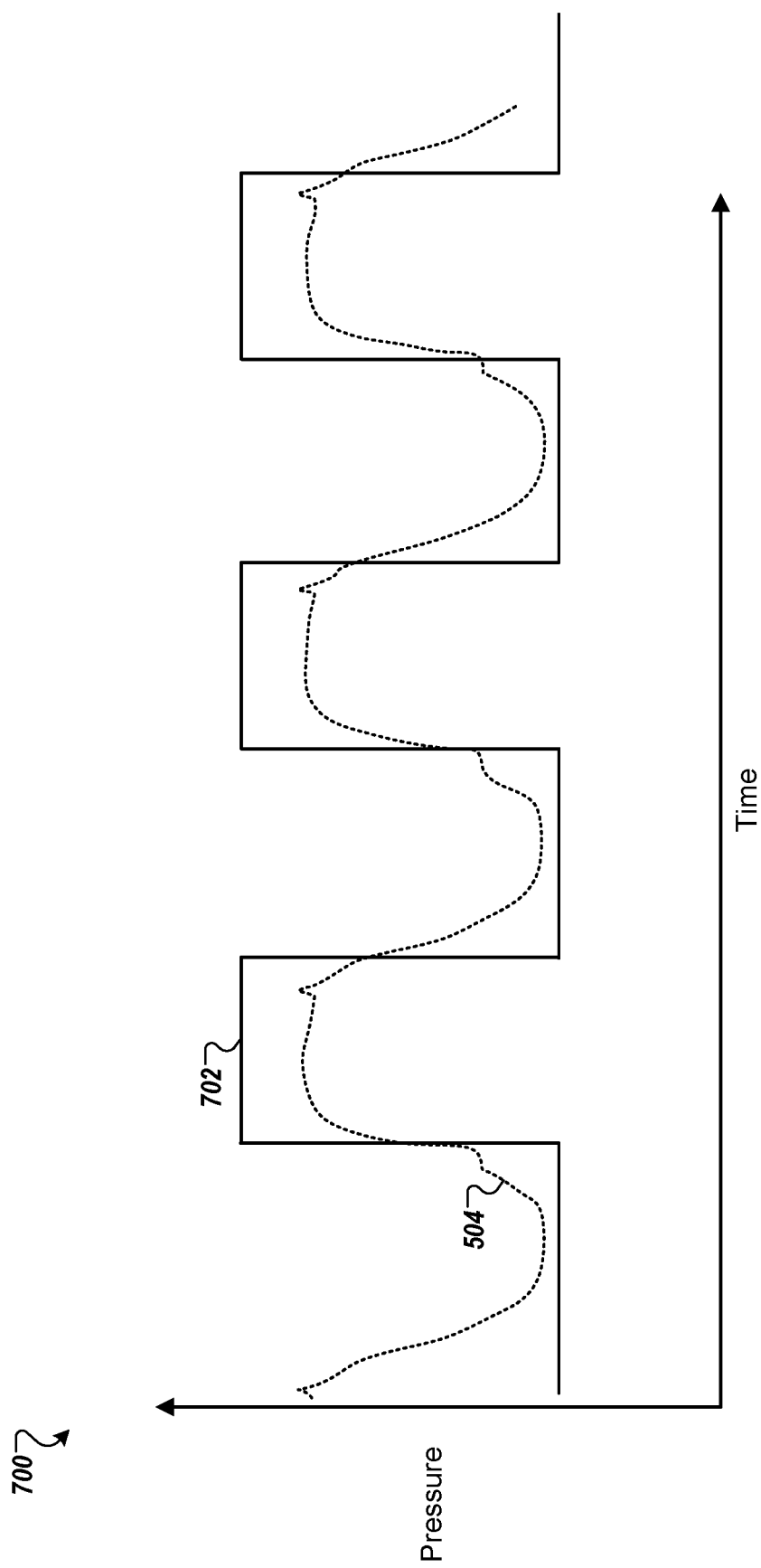
FIG. 7 is a graph showing smoothed pressure readings compared to the threshold that may be used to detect user presence in a bed.

FIGS. 6 and 7 show the instant pressure reading curve 502 and the smoothed curve 504, respectively, along with a presence curve 602 and 702. The presence curves 602 and 702 may be calculated and used by a computing device such as the control circuitry to determine presence in a bed.

In the graphs 600 and 700, the curves 502 and 504 are compared with a threshold value. When the curves 502 or 504 are below the threshold value, the associated presence curves 602 or 702 are set to a low value, and when the curves 502 or 504 are above the threshold value, the associated presence curves 602 or 702 are set to a high value. When the presence curves 602 or 702 are set at the high value, a computing system such as the control circuitry may determine that a user is in the bed, and when the presence curves 602 or 702 are set to a low value, a computing system such as the control circuitry may determine that the user is not in the bed.

The threshold value or values used may be static or dynamically calculated by a computer system. For example, the threshold used for the graph 600 may be the same or different than the threshold used for the graph 700. A computer system may calculate and modify this threshold according to one or more factors. These factors include, but are not limited to, historic user weight information, projected user weight estimates, and seasonality.

As most beds are used by the same user or users most nights, a computing device can build a profile for one or more users of the bed. This profile can include, for example, historic weight information and age information. The weight may be collected from historic pressure readings, including use of the calculations described with respect to graphs 400 and 450. The age information may be generated from, for example, comparing user weights to average weight by age data. Additionally or alternatively, the user age data may be input from an external source such as user profile data from a database or user entry into a computer interface.

Based off this profile, a computer system such as the control circuitry can calculate a threshold value that is greater than the pressure when the user is not in the bed and less than the pressure when the user is in the bed. This threshold value may be adjusted over time, for example, to account for user growth and seasonality.

A child user may increase in weight at a predictable rate, based on historical weight information and age information. As such, the threshold value may be adjusted over time (e.g., on a regular schedule, as spare computing resources are available) to account for the child users growth.

Additionally or alternatively, the threshold value may be adjusted over time to adjust for seasonality. Based on a user's profile, general seasonality rules, and/or other rules, the threshold value may change based on a repeating schedule. This schedule may be yearly to account for the change in seasons and thus changing bedding. Additionally or alternatively, the schedule may be daily or weekly to adjust for user's schedules. For example, consider a bed used by two users. On weeknights both users may normally go to bed at the same time. On these days, a threshold value would account for the two user's combined weight. On weekend nights, the two users may go to bed at different times, and on these days two smaller threshold values may be used instead.

A plurality of user presence tests have been described. Generally, these presence tests can be conducted by a computing system such at the control circuitry. The computer system may implement one test, or may combine the output of more than one test to determine user presence in a bed. An example of such mixing is described below with respect to process 800. In addition, there are other tests for user presence that may be used exclusively or in combination with these or other tests. One such test includes monitoring pressure to detect user heart-rate and/or breathing.

The presence detection may take the form of any technologically appropriate configuration. For example, the presence determination may be a binary resolution, either "True" or "False." In another example, the presence determination may take the form of a probability, confidence value, or other similar record. The computer system may store the presence detection into computer readable memory for access by the computer system and/or for transmission to another computer system.

For example, one process in the computer system may determine user presence and store the presence determination in computer memory. Another process, either running in the computer system or another system, can query that computer memory to receive the presence determination.

Based on the presence determination stored in memory, a computer process may take or abstain from some action or actions. For example, a user may turn on their lights to navigate to their bed, and then enter their bed. Using one or more presence tests, a computer system may determine that the user has entered the bed and store a positive presence detection into computer memory. In response to detecting the positive presence detection, the computer system may issue a command to the user's lighting system 314 to dim and/or turn off the lights. Other actions that may be performed in response to user presence or lack of presence have previously been described with reference to the FIG. 3.

Figure 8:
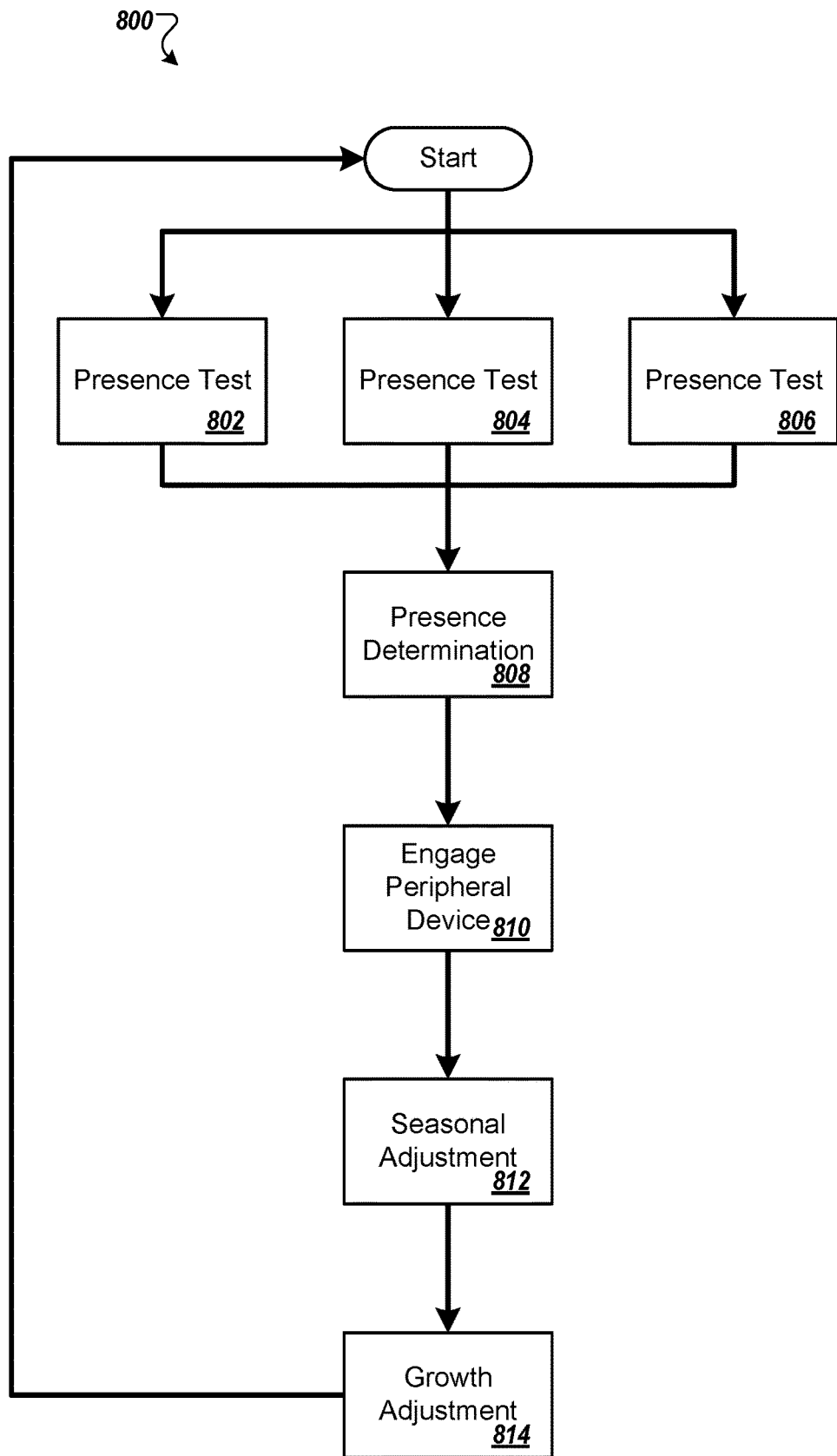
FIGS. 8-10 are flowcharts of processes for determining user presence in a bed.

FIG. 8 is a flowchart of an example process 800 for determining user presence in a bed. In the process 800, three presence tests are performed by a computer device to generate a presence determination. The process 800 may be performed by any technologically appropriate system, including but not limited to the systems described with respect to FIGS. 1-3.

A plurality of presence tests are performed 802-806. For example, the control circuitry of a bed may perform three presence tests. In the first test, a trailing average is compared to instant pressure readings to determine when the trailing average and instant pressure readings converge. In the second test, a smoothed pressure reading is compared to a threshold value to determine when the smoothed pressure reading is greater than a threshold value. In a third test, a signal in pressure readings is identified to indicate that a weight on the bed produces movements consistent with a heartbeat.

A presence determination is made 808. For example, the control circuitry can combine the output of the presence tests 802, 804, 806. In one scheme for combining the presence tests 802, 804, 806, each presence test produces a Boolean 'True' or 'False,' and if two of the three tests return 'True,' a positive presence determination is made.

In another test, each of the three presence tests 802, 804, 806 return a confidence value from 0 to 1. A weighted average of the three confidence values may be found. For example, if test 802 returns a confidence of 0.7 and is given a weight of 0.5, test 804 returns a confidence value of 0.9 and is given a weight of 0.3, and test 806 returns a confidence value of 0.1 and is given a weight of 0.2, the final presence determination 808 may be the sum of the confidence values multiplied by their associated weights, or the sum of 0.7*0.5+0.9*0.3+0.1*0.2, or 0.64 on a scale of 0 to 1.

In yet another test, the tests may be performed in series until a negative test is found. This may be useful, for example, if some tests are computationally intensive, and some other tests may be run to rule out the need for the intensive tests. For example, the trailing average test described with respect to process 900 may be more computationally intensive than a test to detect a heartbeat. In such a case, the heartbeat test may be performed first, and if found positive, the trailing average test may be performed. If the heartbeat test is found to be negative, there may be no need to perform the trailing average test.

A computer readable memory is updated, a computational event is triggered, and a peripheral device is engaged 810. For example, control circuitry may store the presence determination 808 in computer readable memory (e.g., RAM, a hard disk, a network storage location). A computer process monitoring this readable memory may identify that a new presence determination is loaded and raise a computational event. A peripheral device controller may be configured to listen for this computational event and, responsive to detecting the computational event, may engage an associated peripheral device. For example, in response to a determination that a previously occupied bed is no longer occupied, a coffee maker may be turned on. In response to determining that the user has been occupying the bed for more than 8 hours, a lighting control system may slowly increase the lighting in the room.

In some cases, the peripheral device is not engaged until the user presence in the bed is detected for a particular amount of time. For example, the peripheral device may be an under-bed lighting system that is intended to assist the user if they get out of bed in the middle of the night. In such a bed, the user may be a child and a parent may read to the child in for fifteen or twenty minutes at night. In such a scenario, the under-bed lighting may be configured to turn on only if presence is detected for more than an hour. By keeping this delay longer than the time an adult reads in bed, the system will not illuminate the under-bed lighting when the parent exits the bed, thus avoiding a situation where the child should be falling asleep with the light on.

A seasonal adjustment is made 812. For example, in preparation for the next presence tests 802, 804, 806 and/or presence determination 808, a seasonal adjustment 812 to one or more parameters of one or more presence tests 802, 804, 806 and/or the presence determination 808 may be made. For example, a threshold value may be decreased to account for an expected reduction in bedding.

A growth adjustment is made 814. For example, in preparation for the next presence tests 802, 804, 806 and/or presence determination 808, a growth adjustment 814 to one or more parameters of one or more presence tests 802, 804, 806 and/or the presence determination 808 may be made. For example, a threshold value may be increased to account for an expected increase in the user's weight.

Figure 9:
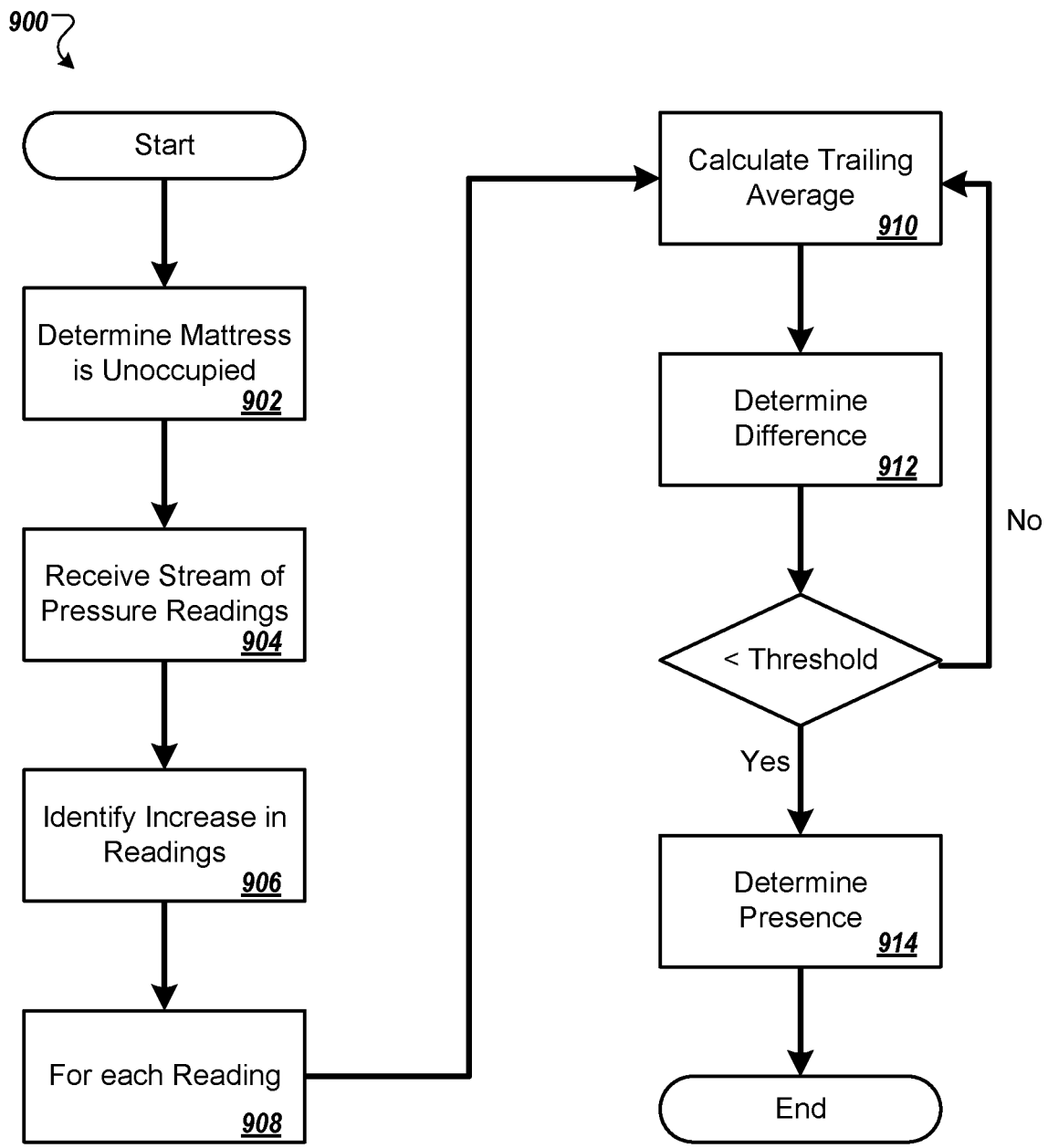

FIG. 9 is a flowchart of an example process 900 for determining user presence in a bed. The process 900 is one example of presence tests 802, 804, 806. The process 900 may be performed by any technologically appropriate system, including but not limited to the systems described with respect to FIGS. 1-3.

A computer device determines that a mattress is unoccupied 902. For example, the computer device may determine that the pressure of the mattress is constant for a period of time, or a previously performed presence test may return a negative result.

A stream of pump pressure readings are received from a mattress pump at the computing device 904. The pump pressure readings record the air pressure of the mattress. For example, the pump of a mattress may include a sensor that detects the air pressure of the mattress. This pump may be configured to report these readings in a stream to a computing device. The stream of data may include, but is not limited to, a reporting of readings on a regular schedule, reporting in response to requests for the reading, and other schemes.

The computing device identifies an increase in pump pressure readings within a time window 906. For example, the computing device may identify that, within a period of time or a number of readings, the value of the readings increases more than a threshold value. This may represent, for example, a sharp increase in air pressure within the mattress.

After identifying the increase in pump pressure readings within the time window and for each received pump pressure readings, the computing device determines that a difference is less than a threshold value 908. For example, until a test generating a difference value returns a difference smaller than a threshold value, the test may be repeated for each received pump pressure value. The test may also be performed on a different sampling frequency (e.g., every other or every third pump pressure value received).

The computing device calculates a trailing average pressure that represents the average of the N most recent pump pressures readings in the stream of pump pressure readings 910. For example, if N=7, the computing device may average the most current pump pressure reading with the six preceding that have been stored in memory.

The computing device determines the difference between the received pump pressure reading and the trailing average pressure 912. For example, the computing device may subtract the trailing average from the received pump pressure reading to determine the difference. That difference is then compared to a threshold value that may be, for example, pre-determined or calculated in response to changing parameters.

Responsive to the computing device determining that the difference is less than the threshold value, presence is determined 914. For example, a value may be stored in computer readable memory to record the presence, a computing event may be raised, and/or a peripheral device may be engaged.

Figure 10:
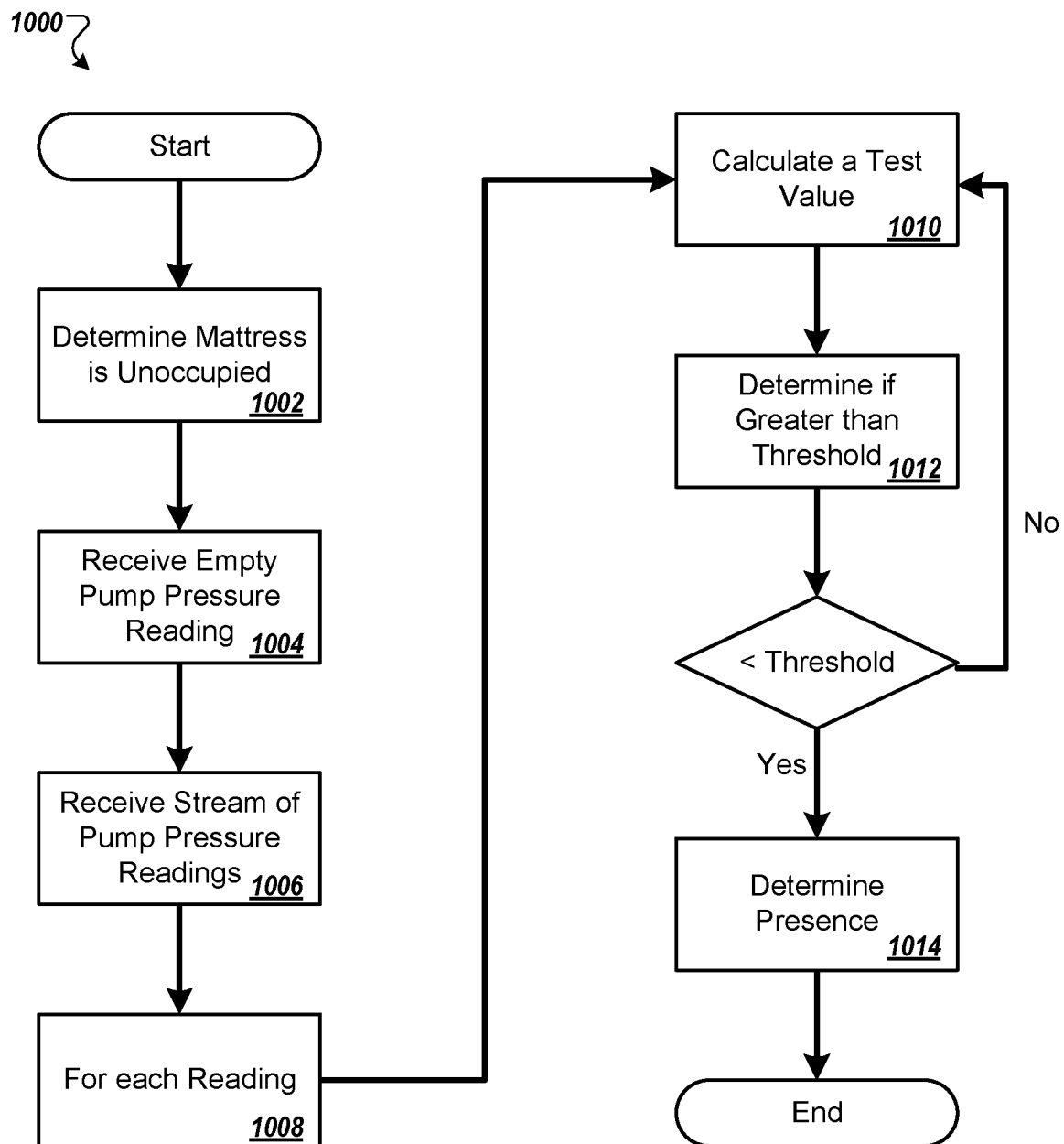

FIG. 10 is a flowchart of an example process 1000 for determining user presence in a bed. The process 1000 is one example presence test 802-806. The process 1000 may be performed by any technologically appropriate system, including but not limited to the systems described with respect to FIGS. 1-3.

A computer device determines that a mattress is unoccupied 1002. For example, the computer device may determine that the pressure of the mattress is constant for a period of time, or a previously performed presence test may return a negative result.

An empty pump pressure reading is received from a mattress pump and at a computing device 1004. The empty pump pressure reading records the air pressure of the mattress when the mattress is not subject to pressure from a person. For example, the computer device may record the constant pressure as the empty pump pressure reading.

A stream of pump pressure readings are received from a mattress pump at the computing device 1006. The pump pressure readings record the air pressure of the mattress when the mattress is subject to pressure from an external body.

For each received pump pressure reading, the computing device performs a test 1008. For example, until a test comparing pressure readings to a threshold value returns true, the test may be repeated for each received pump pressure value. The test may also be performed on a different sampling frequency (e.g., every other or every third pump pressure value received).

The computing device calculates a test value that includes the most recent pump pressure reading in the stream of pump pressure readings 1010. For example, the test value may be the most recent pump pressure value, a weighted or weighted average, and/or a smoothed value.

The computing device determines that the test value is greater than a threshold value that is greater than the empty pump pressure reading 1012. For example, if the test value is 2382 and the threshold value is 1849, the computing device determines that the test value is greater.

Responsive to the computing device determining that the difference is less than the threshold value, presence is determined 1014. For example, a value may be stored in computer readable memory to record the presence, a computing event may be raised, and/or a peripheral device may be engaged.

Figure 11:
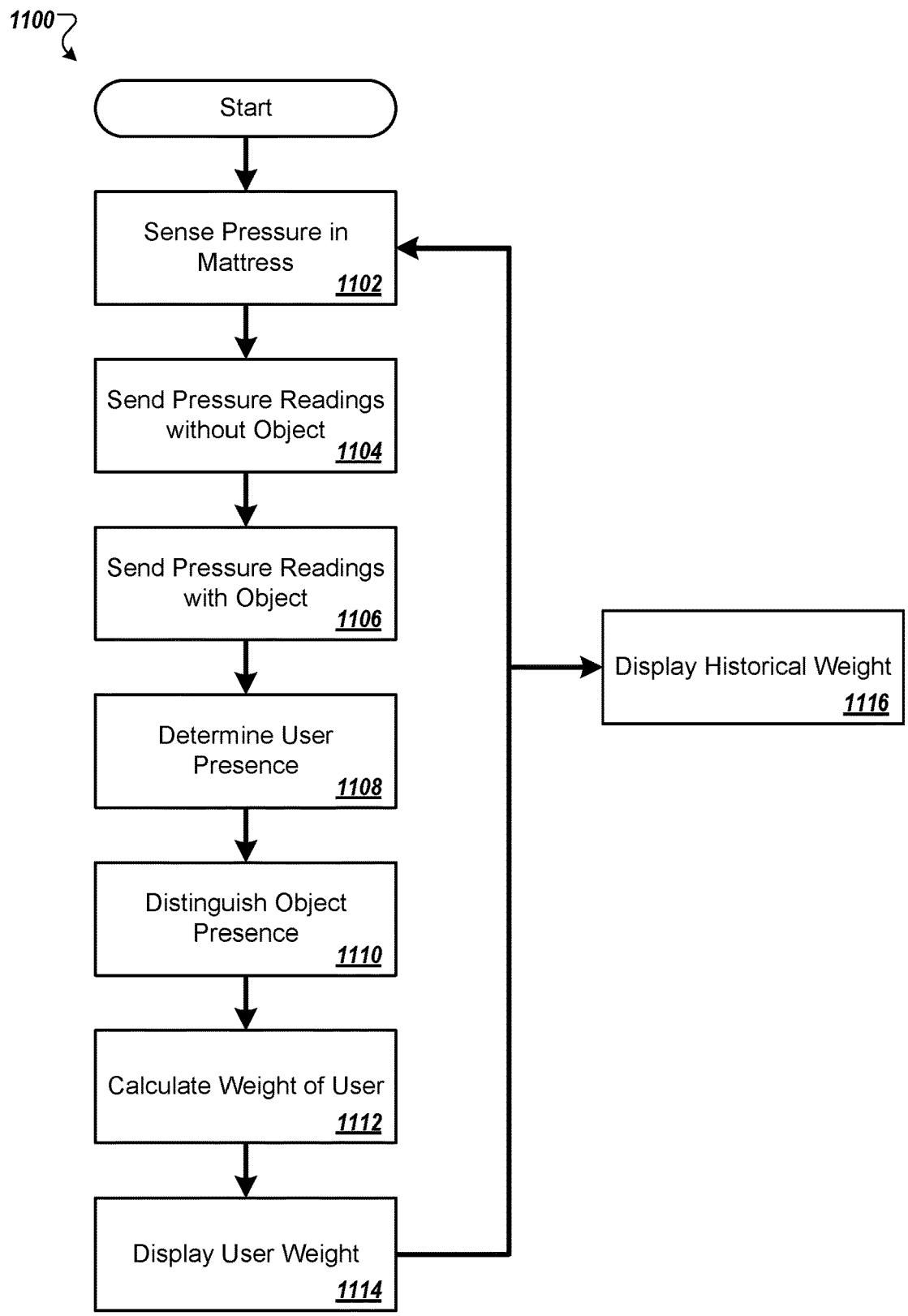
FIG. 11 is a flowchart of a process for tracking the growth of a user.

FIG. 11 is a flowchart of a process for tracking the growth of a user. The process 1000 may be performed by any technologically appropriate system, including but not limited to the systems described with respect to FIGS. 1-3.

Pressure in an air bladder of a mattress of a bed is sensed via a bed pressure sensor in fluid communication with the air bladder 1102. For example, a sensor continuously or non-continuously samples the pressure of one or more air bladders on the bed. That sampling is converted into a digital computer signal for transmission.

A first stream of pressure readings are sent from the bed pressure sensor to a computing device 1104. For example, while a user is laying on the bed, the bed sensor sends a stream of pressure readings to a computing device. These pressure readings may be transmitted in any appropriate format, including but not limited to transmission on a regular interval or in response to requests for readings.

A second stream of pressure readings are sent from the bed pressure sensor to the computing device 1106. The second stream of pressure readings include the influence of one or more objects on the bed. For example, an additional object may be placed on the bed with the user. The user may add an extra blanket to their bedding, or a second user may enter the bed.

The user presence on the mattress is determined via the computing device and the first stream of pressure readings 1108. For example, using one or more tests described in this document or other test or tests, the computing device may determine user presence in the bed.

The computing device distinguishes the first stream of pressure readings as indicative of a user present on the mattress from the second stream of readings as indicative of one or more objects other than the user being present on the mattress 1110, such as a blanket, stuff animal, suitcase, etc. For example, the computing device may detect a sharp increase in pressure and determine that an additional object has been added to the bed.

A first weight of the user is calculated via the computing device and the first stream of pressure readings 1112. The calculation is performed by excluding the weight changes due to the one or more other objects other than the user. In some implementations, the computing device may be configured to perform one or more mathematical functions that uses the pressure as an input value and provides weight as an output value. In another example, the computing device may look up a weight value on a look-up table using the pressure as the look-up key.

A signal indicative of user weight is sent to a user interface to be displayed as in indicia of user weight by the user interface 1114. For example, the weight value may be stored in computer memory, optionally in association with a computer-recorded profile of the user. A computing device may read this computer memory to receive the weight of the user and display it to the user or another user.

Historical weight is displayed 1116. The weight tracking is repeated over a plurality of days and the output shows the weight of the user over the plurality of days. This historic data may be stored in computer memory and displayed. Historical weight data can be displayed as a chart or graph, such as a bar graph or a line graph. In one example, historical weight can be displayed by displaying a representation of the user's weight daily over a period of time, such as a week, a month, a year, or several years. This can allow a user to track his or her weight (or can allow a parent or family member to track the user's weight) on a daily basis without requiring the user or family member to take any extra action other than going to bed nightly. In another example, historical weight can be displayed by displaying a representation of the user's weight periodically (such as weekly or monthly) over a period of time (such as over a month, over several months, over a year, or over several years). This can allow the user to track his or her weight (or can allow a parent or family member to track the user's weight) on a regular basis without requiring the user or family member to take any extra action other than going to bed. In another example, historical weight data can be displayed by displaying a single weight (or multiple weight) corresponding to specific dates or date ranges. In some examples, tracking user weight via the bed system can allow a user to assess the effects of past lifestyle changes (e.g. exercise, sleep patterns, eating habits) on the user's weight. In some examples, tracking user weight via the bed system can help a medical professional examine a user's health and/or diagnose health conditions by reviewing weight data that may not be available for typical patients.

The computing device adjusts for weight changes due to the inanimate objects being placed on and removed from the mattress so as to omit weight changes due to inanimate objects from the historical weight data outputted via the user interface. For example, if a four pound animal is known by the computing device to lay on the bed, four pound sudden increases in user weight may be excluded to account for the animal.

Although a particular number, order, and types of steps are described, different numbers, orders, and types of steps may be used in these and similar processes.

Figure 12:
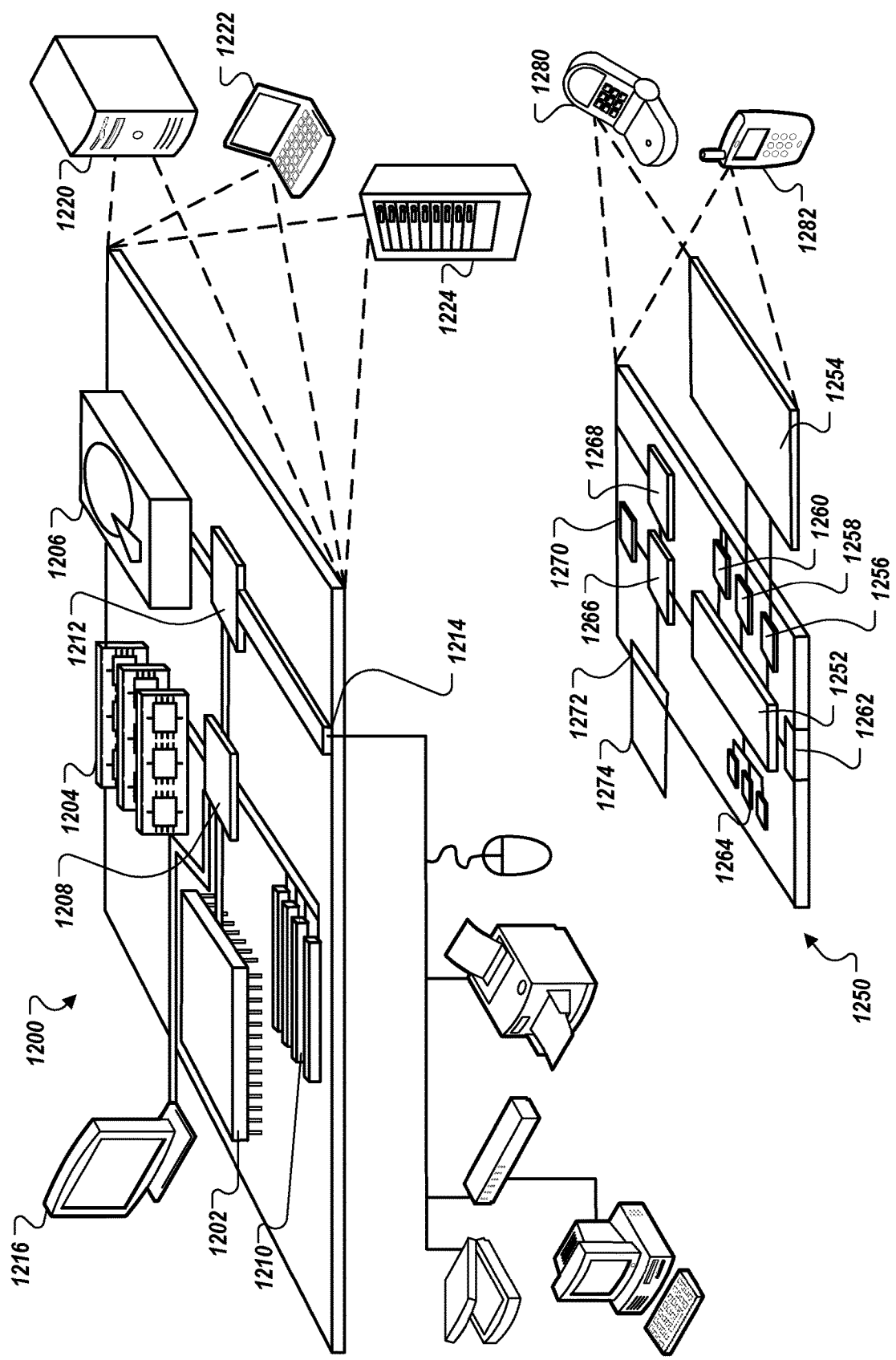
FIG. 12 is a schematic diagram that shows an example of a computing device and a mobile computing device.

FIG. 12 is a schematic diagram that shows an example of a computing device and a mobile computing device. FIG. 12 shows an example of a computing device 1200 and an example of a mobile computing device that can be used to implement the techniques described here. The computing device 1200 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1204 stores information within the computing device 1200. In some implementations, the memory 1204 is a volatile memory unit or units. In some implementations, the memory 1204 is a non-volatile memory unit or units. The memory 1204 may also be another form of computer-readable medium, such as a magnetic or optical disk.

The storage device 1206 is capable of providing mass storage for the computing device 1200. In some implementations, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The computer program product can also be tangibly embodied in a computer- or machine-readable medium, such as the memory 1204, the storage device 1206, or memory on the processor 1202.

The high-speed interface 1208 manages bandwidth-intensive operations for the computing device 1200, while the low-speed interface 1212 manages lower bandwidth-intensive operations. Such allocation of functions is exemplary only. In some implementations, the high-speed interface 1208 is coupled to the memory 1204, the display 1216 (e.g., through a graphics processor or accelerator), and to the high-speed expansion ports 1210, which may accept various expansion cards (not shown). In the implementation, the low-speed interface 1212 is coupled to the storage device 1206 and the low-speed expansion port 1214. The low-speed expansion port 1214, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. In addition, it may be implemented in a personal computer such as a laptop computer 1222. It may also be implemented as part of a rack server system 1224. Alternatively, components from the computing device 1200 may be combined with other components in a mobile device (not shown), such as a mobile computing device 1250. Each of such devices may contain one or more of the computing device 1200 and the mobile computing device 1250, and an entire system may be made up of multiple computing devices communicating with each other.

The mobile computing device 1250 includes a processor 1252, a memory 1264, and an input/output device such as a display 1254, a communication interface 1266, and a transceiver 1268, among other components. The mobile computing device 1250 may also be provided with a storage device, such as a micro-drive or other device, to provide additional storage. Each of the processor 1252, the memory 1264, the display 1254, the communication interface 1266, and the transceiver 1268, are interconnected using various buses, and several of the components may be mounted on a common motherboard or in other manners as appropriate.

The processor 1252 can execute instructions within the mobile computing device 1250, including instructions stored in the memory 1264. The processor 1252 may be implemented as a chipset of chips that include separate and multiple analog and digital processors. The processor 1252 may provide, for example, for coordination of the other components of the mobile computing device 1250, such as control of user interfaces, applications run by the mobile computing device 1250, and wireless communication by the mobile computing device 1250.

The processor 1252 may communicate with a user through a control interface 1258 and a display interface 1256 coupled to the display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may provide communication with the processor 1252, so as to enable near area communication of the mobile computing device 1250 with other devices. The external interface 1262 may provide, for example, for wired communication in some implementations, or for wireless communication in other implementations, and multiple interfaces may also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 may also be provided and connected to the mobile computing device 1250 through an expansion interface 1272, which may include, for example, a SIMM (Single in Line Memory Module) card interface. The expansion memory 1274 may provide extra storage space for the mobile computing device 1250, or may also store applications or other information for the mobile computing device 1250. Specifically, the expansion memory 1274 may include instructions to carry out or supplement the processes described above, and may include secure information also. Thus, for example, the expansion memory 1274 may be provided as a security module for the mobile computing device 1250, and may be programmed with instructions that permit secure use of the mobile computing device 1250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1264, the expansion memory 1274, or memory on the processor 1252. In some implementations, the computer program product can be received in a propagated signal, for example, over the transceiver 1268 or the external interface 1262.

The mobile computing device 1250 may communicate wirelessly through the communication interface 1266, which may include digital signal processing circuitry where necessary. The communication interface 1266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1268 using a radio-frequency. In addition, short-range communication may occur, such as using a Bluetooth, WiFi, or other such transceiver (not shown). In addition, a GPS (Global Positioning System) receiver module 1270 may provide additional navigation- and location-related wireless data to the mobile computing device 1250, which may be used as appropriate by applications running on the mobile computing device 1250.

The mobile computing device 1250 may also communicate audibly using an audio codec 1260, which may receive spoken information from a user and convert it to usable digital information. The audio codec 1260 may likewise generate audible sound for a user, such as through a speaker, e.g., in a handset of the mobile computing device 1250. Such sound may include sound from voice telephone calls, may include recorded sound (e.g., voice messages, music files, etc.) and may also include sound generated by applications operating on the mobile computing device 1250.

The mobile computing device 1250 may be implemented in a number of different forms, as shown in the figure. For example, it may be implemented as a cellular telephone 1280. It may also be implemented as part of a smart-phone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be a special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

What is claimed is:

1. A method performed by data processing apparatuses, the method comprising:
    determining, by a computing device, that a mattress of a bed is unoccupied;
    receiving, from a mattress pump and at a computing device, an empty pump pressure reading, the empty pump pressure reading recording air pressure of the mattress when the mattress is not subject to pressure from a person;
    receiving, from the mattress pump and at a computing device, a stream of pump pressure readings, the pump pressure readings recording air pressure of the mattress when the mattress is subject to pressure from an external body;
    for each received pump pressure readings:
        calculating, by the computing device, a test value that includes the most recent pump pressure reading in the stream of pump pressure readings; and
        determining, by the computing device, if the test value is greater than a threshold value that is greater than the empty pump pressure reading; and
    responsive to the computing device determining that the test value is greater than the threshold value, engaging a peripheral device.

2. The method of claim 1, wherein the test value is a trailing average pressure that represents the average of the N most recent pump pressure readings in the stream of pump pressure readings.

3. The method of claim 1, the method further comprising:
    identifying, based on the stream of pump pressure readings, a supplemental indication of presence in the bed; and
    wherein, responsive to the computing device determining that the test value is greater than the threshold value, engaging a peripheral device further comprises:
        combining the supplemental indication of presence in the bed with the determining that the difference is significant compared to the threshold value.

4. The method of claim 3, wherein the supplemental indication of presence in the bed comprises identifying biological activity by an occupant of the bed.

5. The method of claim 1, the method further comprising modifying the threshold value.

6. The method of claim 5, wherein the threshold value is modified to account for seasonality.

7. The method of claim 5, wherein the threshold value is modified to account for growth of the user.

8. The method of claim 1, the method further comprising updating a user-facing computer interface to show that a user is detected in the bed.

9. The method of claim 1, wherein engaging a peripheral device comprises engaging an under-bed lighting system.

10. The method of claim 1, wherein:
    the computing device comprises a controller having a computing processor and computing memory, the controller being physically couplable to the bed; and
    the pump comprises:

a motor configured to be energized in response to a command to increase pressure of the mattress; and a pressure transducer configured to sense air-pressure of the mattress;

wherein the pump is in fluid communication with at least one air chamber of the mattress.

11. A controller configured to:

determine that a mattress is unoccupied;

receive, from a mattress pump, an empty pump pressure reading, the empty pump pressure reading recording air pressure of the mattress when the mattress is not subject to pressure from a person;

receive, from the mattress pump, a stream of pump pressure readings, the pump pressure readings recording air pressure of the mattress when the mattress is subject to pressure from an external body;

for each received pump pressure readings:
  calculate a test value that includes the most recent pump pressure reading in the stream of pump pressure readings; and
  determine if the test value is greater than a threshold value that is greater than the empty pump pressure reading; and responsive to determining that the test value is greater than the threshold value, engage a peripheral device.

12. The controller of claim 11, wherein the test value is a trailing average pressure that represents the average of the N most recent pump pressure readings in the stream of pump pressure readings.

13. The controller of claim 11, wherein the controller is further configured to:

identify, based on the stream of pump pressure readings, a supplemental indication of presence in the bed; and wherein, responsive to determining that the test value is greater than the threshold value, engaging a peripheral device further comprises:

combining the supplemental indication of presence in the bed with the determining that the difference is significant compared to the threshold value.

14. The controller of claim 13, wherein the supplemental indication of presence in the bed comprises identifying biological activity by an occupant of the bed.

15. The controller of claim 11, wherein the controller is further configured to modify the threshold value.

16. The controller of claim 15, wherein the threshold value is modified to account for seasonality.

17. The controller of claim 15, wherein the threshold value is modified to account for growth of the user.

18. The controller of claim 11, wherein the controller is further configured to update a user-facing computer interface to show that a user is detected in the bed.

19. The controller of claim 11, wherein engaging a peripheral device comprises engaging an under-bed lighting system.

20. The controller of claim 11, wherein:

the controller comprises a computing processor and computing memory, the controller being physically couplable to the bed; and the pump comprises:
  a motor configured to be energized in response to a command to increase pressure of the mattress; and
  a pressure transducer configured to sense air-pressure of the mattress;

wherein the pump is in fluid communication with at least one air chamber of the mattress.

* * * * *